(12) United States Patent
Penner et al.

(10) Patent No.: US 6,622,049 B2
(45) Date of Patent: Sep. 16, 2003

(54) MINIATURE IMPLANTABLE ILLUMINATOR FOR PHOTODYNAMIC THERAPY

(75) Inventors: Avl Penner, Tel Aviv (IL); Eyal Doron, Kiryat Yam (IL)

(73) Assignee: Remon Medical Technologies Ltd., Caesarea (IL)

( * ) Notice: Subject to any disclaimer, the term of this patent is extended or adjusted under 35 U.S.C. 154(b) by 0 days.

(21) Appl. No.: 10/066,799

(22) Filed: Feb. 6, 2002

(65) Prior Publication Data

US 2003/0074034 A1 Apr. 17, 2003

Related U.S. Application Data

(63) Continuation-in-part of application No. PCT/IL01/00951, filed on Oct. 15, 2001.

(51) Int. Cl.[7] .................................................. A61N 1/08

(52) U.S. Cl. .............................. 607/59; 607/1; 607/88; 607/30; 607/33; 607/61; 600/1; 600/3

(58) Field of Search ................................ 607/59, 60, 1, 607/2, 92, 96, 88, 32, 30, 31, 33, 61, 138; 128/898, 899, 903; 600/1, 2, 3; 604/19, 22; 606/201, 2, 3

(56) References Cited

U.S. PATENT DOCUMENTS

| 3,672,352 A | * | 6/1972 | Summers ..................... 607/33 |
| 4,616,640 A | * | 10/1986 | Kaali et al. .................. 607/138 |
| 4,651,740 A | * | 3/1987 | Schroeppel ................... 607/31 |
| 5,749,909 A | * | 5/1998 | Schroeppel et al. .......... 607/33 |
| 6,162,238 A | * | 12/2000 | Kaplan et al. ............... 606/201 |
| 6,239,724 B1 | * | 5/2001 | Doron et al. ................ 128/903 |
| 6,431,175 B1 | * | 8/2002 | Penner et al. ............... 129/899 |

* cited by examiner

Primary Examiner—Teresa Walberg
Assistant Examiner—Fadi H. Dahbour
(74) Attorney, Agent, or Firm—G. E. Ehrlich (1995) Ltd.

(57) ABSTRACT

A miniature implantable light source for providing light to an internal treatment site to effect a photodynamic therapy at the site, the light source is powered and/or controlled via acoustic energy transmitted from outside the body to an acoustic transducer in the light source.

190 Claims, 11 Drawing Sheets

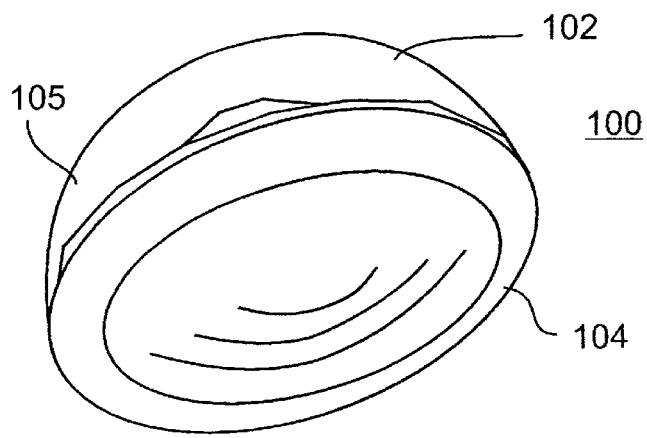
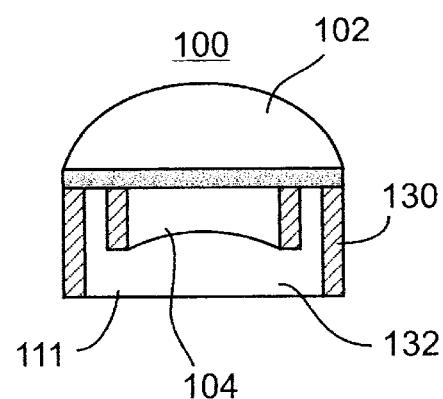
Fig. 7a   Fig. 7b
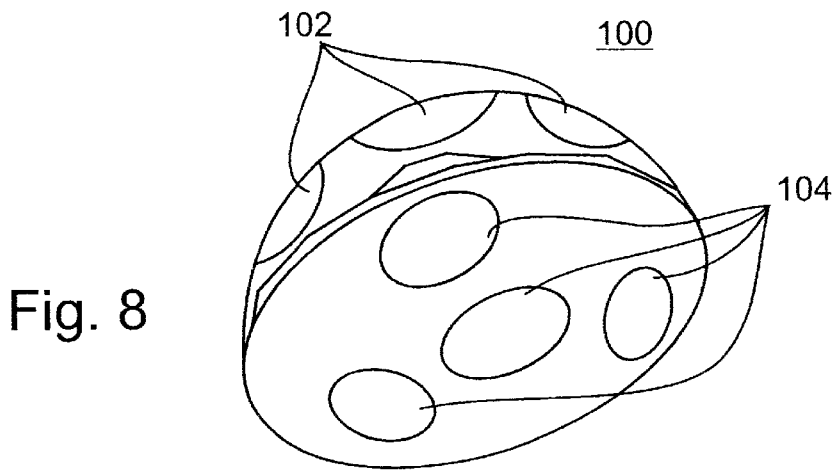
Fig. 8
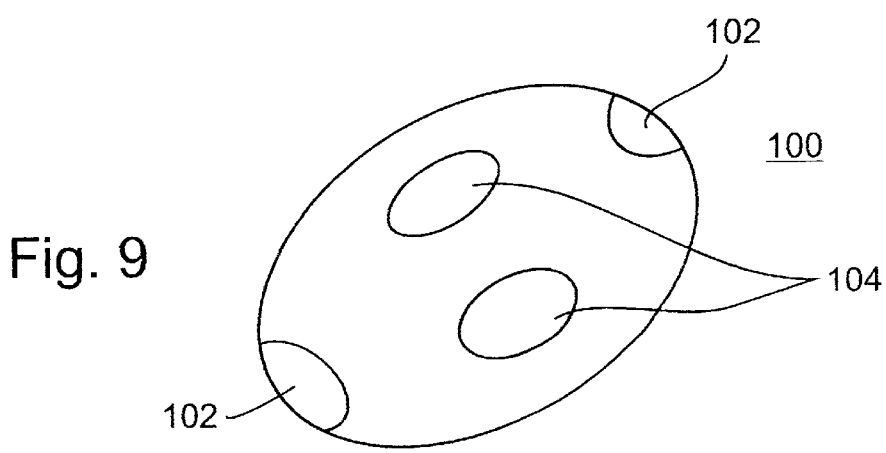
Fig. 9

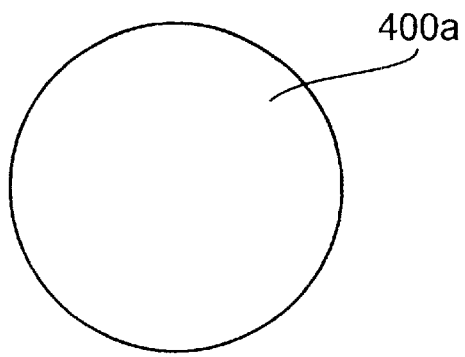
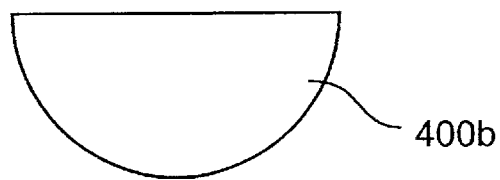
Fig. 15a  Fig. 15b
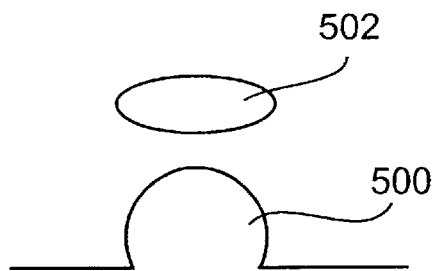
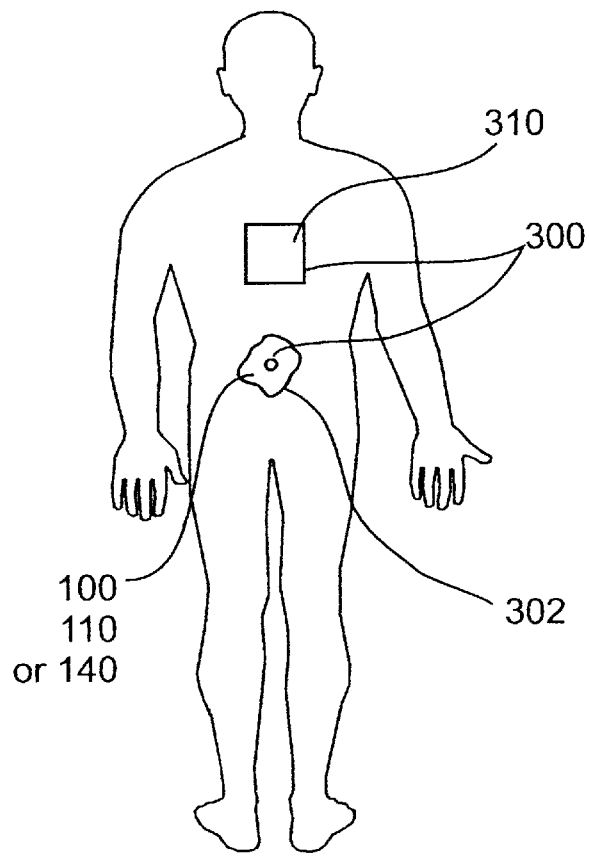
Fig. 16  Fig. 17

MINIATURE IMPLANTABLE ILLUMINATOR FOR PHOTODYNAMIC THERAPY

This is a Continuation-In-Part of PCT/IL01/00951, filed Oct. 15, 2001, which claims the benefit of priority from U.S. patent application Ser. No. 09/690,615, filed Oct. 16, 2000, the specifications of which are hereby incorporated by reference.

FIELD AND BACKGROUND OF THE INVENTION

The present invention is generally directed to a miniature light source for administering photodynamic therapy (PDT), a system incorporating same, and a method for providing such treatment, and more specifically, pertains to an minimal invasively implantable miniature light source which is operably coupled to a power supply that is either acoustically energized or acoustically activated to operate, and to a method for using such a miniature light source to administer PDT.

A tumor comprising abnormal cells is known to selectively absorb certain dyes perfused into the site to a much greater extent than surrounding tissue. For example, compared to normal cells, intracranial gliomas absorb up to a 28 times as much dye. Once pre-sensitized by dye tagging in this manner, the cancerous or abnormal cells can be destroyed by irradiation with light of an appropriate wavelength, several discrete wavelengths or waveband corresponding to an absorbing wavelength, several discrete wavelengths or waveband of the dye, with minimal damage to normal tissue. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors, and for destroying pathogens. Because PDT may be selective in destroying abnormal cells that have absorbed more of the dye, it can successfully be used to kill malignant tissue or organisms with less effect on surrounding benign tissue in the brain and other critical areas.

Typically, invasive applications of PDT have been used during surgical procedures employed to gain access to a treatment site inside the body of the patient. Relatively high intensity light sources have traditionally been used to reduce the duration of the treatment, and thus the time required for the surgery used to expose the treatment site, and because the majority of the prior art teaches that very high intensity light will more likely kill all of the malignant cells. Optical fibers in a hand-held probe are often used to deliver the intense light to the surgically exposed treatment site from a remote light source to reduce damage to surrounding tissue from the heat developed by the light source. High power lasers or solid-state laser diode (LD) arrays in a remote light source coupled to the optical fibers are normally used. A typical prior art light source for PDT would provide from about 0.10 watts to more than 1.0 watts of optical power to achieve the high intensity, short duration exposures that are preferred. Because of the relatively high light intensity and power required to achieve it, apparatus to provide PDT is often physically too large and too heavy to be readily moved about with the patient.

The theoretical basis behind PDT is that the light energy absorbed by dye molecules in the malignant or pathogen cells is transferred to dissolved oxygen to produce a reactive species called "singlet oxygen." This highly reactive form of oxygen kills cancer cells, damages tumor vasculature, and can destroy viruses and bacteria. Since the concentration of dissolved oxygen in cells is comparatively low, it is possible that after all available oxygen is activated and/or reacted with the cell materials, any additional increase in light intensity will have a negligible incremental effect on the tumor or in killing malignant cells. The limiting factor on the rate of malignant cell death in PDT may well be the rate at which additional oxygen diffuses into the treatment site from surrounding tissue and through replenishment via the vascular system. Contrary to the teachings of most of the prior art, the effectiveness of each photon of light impacting the treatment area may be highest at very low light intensities, provided over extended treatment times, and the optical efficiency may in fact decrease with increasing exposure level.

Several researchers, including Haas et al, "Photodynamic Effects of Dyes on Bacteria" Published in Mutation Researchh, 1979, vol. 60, pp. 1–11, have shown that the level of cytotoxicity in PDT appears to be proportional to the product of the integrated light exposure and the photoreactive agent's concentration, rather than to the instantaneous light intensity. In other words, the degree of PDT response is dominated by the total amount of light absorbed by the photoreactive agent over the treatment period. It can therefore be argued that if: (i) the photoreactive agent's concentration in the target tissue is maintained at a therapeutic level; and (ii) apparatus for delivering light of the proper wavelength, several discrete wavelengths or waveband to a treatment site over an extended period is available, then the benefits of PDT can be realized with a less aggressive and potentially less costly treatment carried out over a period ranging from days to weeks. Longer treatment periods at lower dosage rates may have other benefits as well, since high dosage rates continued over extended periods can result in adverse normal tissue response.

Maintenance of therapeutic photoreactive agent levels at a treatment site in the body is not difficult. It is well known that many PDT photoreactive agents have a long half-life in the human body. In some cases, however, it is necessary for a patient to avoid direct sunlight for up to 30 days to avoid sunburn or phototoxic side effects of the photoreactive agents that are infused into the body.

Teachings in the prior art have shown that it is possible, in certain cases, to obtain improved therapeutic results in PDT at a low light level. As reported by J. A. Parrish in "Photobiologic Consideration in Photoradiation Therapy," pp. 91–108, Porphyrin Photosensitization, Plenum Press, (1983), preliminary laboratory studies with hematoporphyrin and visible light suggest that the reciprocity effect does not always hold, and that low light intensity may be more effective in PDT, in an absolute sense. In these experiments, subcutaneous tumors in the flanks of newborn rats were treated with the same external dose of 620 nm radiation at intensities of 7.5, 28, and 75 mW/cm$^2$. At the same total light dosage, Parrish found that greater tumor necrosis occurred at the lowest light intensity used.

In addition, several researchers have shown that combinations of certain photoreactive agents and low light levels exhibit very potent cytotoxicity. Some studies have shown that more than 99% of gram-positive *Staphylococcus aureus* and *Streptococcus faecalis* bacterial cultures can be killed with the application of 5$^2$ mW/cm of broad band light from a tungsten bulb for 30 minutes, if the cultures are initially dosed with 1–10 micrograms/ml of deuteroporphyrin. Continued application of light for ten to eleven hours results in a sterile condition in the culture, i.e., no bacteria remain alive.

Labrousse and Satre "Photodynamic Killing of Dictyostelium discoideum Amoebae Mediated by 4',5'-Diiodoflurescin Isothiocyanate Dextran. A strategy for the isolation of Thermoconditional Endocytosis Mutants", published in Photochemistry and Photobiology, 1993, vol. 67, No. 3, pp. 531–537, have demonstrated a similar photodynamic extermination of amoebae when dosed with low concentrations of 4'5'-Diiodofluorescein isothiocyanate dextran and irradiated for about 30 minutes with broad band light of 8–10 mW/cm$^2$ from a tungsten lamp. Both of these experimental results are particularly significant because the fraction of a tungsten lamp's output energy that can be absorbed by either photoreactive agent is small, since each agent has a narrow absorbance waveband.

For all PDT light sources, the vast majority of the optical power delivered to tissue eventually degrades to heat. From a therapy perspective, it is likely that this heat load will augment the treatment due to improved chemical reaction rates at higher tissue temperatures. It is also true that cells kept above approximately 43° C. are not viable. This effect is, in fact, used in the treatment of cancer using hyperthermia. In that situation, an attempt is made to heat the target tumor with radio frequency (RF) energy to a temperature on the order of 43° C.–45° C., while maintaining surrounding healthy tissue below 43° C. Combining hyperthermia with conventional transcutaneous PDT has been shown by B. Henderson et al. to increase the efficacy of both treatments (see "Interaction of Photodynamic Therapy and Hyperthermia: Tumor Response and Cell Survival after Treatment of Mice in Vivo," Cancer Research, Vol. 45, 6071 (December 1985)). Combining hyperthermia treatment with PDT delivered, for example, by an implantable probe in accordance with the present invention, will very likely augment the effects of either treatment used alone in destroying tumors.

In an attempt to solve the limitations associated with prior art PDT protocols, Chen et al. describe in U.S. Pat. Nos. 5,571,152; 5,800,478, 5,445,608 and 6,273,904 and International application WO 99/66988, which are incorporated herein by reference, intrabody implantable light sources (either LEDs or LDs), which, in the preferred embodiments, are powered by electromagnetic induction using several coil receivers in which an external (extracorporeal) RF transmitter unit induces current, or in other embodiments are operated by a thin polymer battery controlled by pressure, light, radio signal or magnetic field.

It is well known in the art of electromagnetic field transmission and receptions that the higher the frequency of an electromagnetic field is the smaller the antenna that efficiently receives such an electromagnetic field should be, and vice versa, i.e., the lower the frequency of the electromagnetic field is the larger the antenna that efficiently receives such an electromagnetic field should be.

It is also well recognized in the art that body tissues far efficiently absorb high frequency electromagnetic fields as compared to low frequency electromagnetic fields.

Thus, the implants of Chen et al. can use high frequency electromagnetic induction and maintain small antenna size provided that they are implanted close to the skin and not deep within the body. Implanting an implant as taught by Chen et al. deeper within the body calls for lower frequency electromagnetic induction and hence larger antennas, in the range of several centimeters in diameter, which prevents implantation via a minimal invasive procedure, such as catheterization or injection, and calls for a fully invasive surgery, with all its associated limitations ranging from trauma, long hospitalization, discomfort and complications, including infections.

There is thus a widely recognized need for, and it would be highly advantageous to have, a miniature implantable light source for effecting PDT, devoid of the above limitations.

SUMMARY OF THE INVENTION

According to one aspect of the present invention there is provided a miniature light source for providing light to an internal treatment site to effect a photodynamic therapy at the site, comprising: (a) a source of light that produces light of a desired wavelength, several discrete wavelengths or waveband when energized by an electrical current; (b) an energy storage device operably coupled via an electrical circuit to the source of light; (c) a switch operably coupled to the electrical circuit and the energy storage device; and (d) an acoustic transducer coupled to the switch, the acoustic transducer being activatable upon acoustic excitation by an external acoustic energy source for closing the switch to allow current flow from the energy storage device to the source of light.

According to another aspect of the present invention there is provided a system for providing light of a desired wavelength, several discrete wavelengths or waveband to a treatment site disposed internally within a patient's body, to effect a photodynamic therapy of the treatment site, comprising: (a) a miniature light source which comprises: (i) a source of light that produces light of a desired wavelength, several discrete wavelengths or waveband when energized by an electrical current; (ii) an energy storage device operably coupled via an electrical circuit to the source of light; (iii) a switch operably coupled to the electrical circuit and the energy storage device; and (iv) an acoustic transducer coupled to the switch, the acoustic transducer being activatable upon acoustic excitation by an external acoustic energy source for closing the switch to allow current flow from the energy storage device to the source of light; and (b) the external acoustic energy source for activating the acoustic transducer.

According to yet another aspect of the present invention there is provided a method for providing light of a desired wavelength, several discrete wavelengths or waveband to an internal treatment site to effect a photodynamic therapy, comprising: (a) providing a miniature light source which comprises: (i) a source of light that produces light of a desired wavelength, several discrete wavelengths or waveband when energized by an electrical current; (ii) an energy storage device operably coupled via an electrical circuit to the source of light; (iii) a switch operably coupled to the electrical circuit and the energy storage device; and (iv) an acoustic transducer coupled to the switch, the acoustic transducer being activatable upon acoustic excitation by an external acoustic energy source for closing the switch to allow current flow from the energy storage device to the source of light; (b) implanting the miniature light source at the internal treatment site of a subject in need thereof; and (c) activating the acoustic transducer via the external acoustic energy source, thereby providing the light of the desired wavelength, several discrete wavelengths or waveband to the internal treatment site to effect the photodynamic therapy.

According to further features in preferred embodiments of the invention described below, the switch is configured such that the switch is closed only when the acoustic transducer receives a first acoustic excitation signal followed by a second acoustic excitation signal, the first and second acoustic excitation signals being separated by a predetermined delay.

According to still further features in the described preferred embodiments the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

According to still further features in the described preferred embodiments the energy storage device comprises a battery.

According to still further features in the described preferred embodiments the miniature light source is designed and operable to generate light pulses.

According to still further features in the described preferred embodiments the battery is a lithium battery.

According to still further features in the described preferred embodiments the energy storage device comprises a rechargeable device, such as a rechargeable battery or a capacitor, the rechargeable device being rechargeable by a device external to the body.

According to still further features in the described preferred embodiments the acoustic transducer is configured for receiving a first acoustic excitation signal followed by a second acoustic excitation signal, the electrical circuit configured for interpreting the second acoustic excitation signal as one of a predetermined set of commands.

According to still another aspect of the present invention there is provided a miniature light source for providing light to an internal treatment site to effect a photodynamic therapy at the site, comprising (a) a source of light that produces light of a desired wavelength, several discrete wavelengths or waveband when energized by an electrical current; (b) an acoustic transducer being operably coupled via an electrical circuit to the source of light, the acoustic transducer being powered by acoustic energy providable by an external acoustic energy source to effect current flow to the source of light.

According to a preferred embodiment of this aspect of the present invention, the miniature light source, further comprising a capacitor in said electrical circuit, the capacitor being chargeable by the acoustic transducer and dischargeable so as to effect the current flow to the source of light.

According to an additional aspect of the present invention there is provided a system for providing light of a desired wavelength, several discrete wavelengths or waveband to a treatment site disposed internally within a patient's body, to effect a photodynamic therapy of the treatment site, comprising: (a) a miniature light source which comprises: (i) a source of light that produces light of a desired wavelength, several discrete wavelengths or waveband when energized by an electrical current; and (ii) an acoustic transducer being operably coupled via an electrical circuit to the source of light, the acoustic transducer being powered by acoustic energy providable by an external acoustic energy source to effect current flow to the source of light; and (b) the external acoustic energy source for activating the acoustic transducer.

According to yet an additional aspect of the present invention there is provided a method for providing light of a desired wavelength, several discrete wavelengths or waveband to an internal treatment site to effect a photodynamic therapy, comprising: (a) providing a miniature light source which comprises: (i) a source of light that produces light of a desired wavelength, several discrete wavelengths or waveband when energized by an electrical current; and (ii) an acoustic transducer being operably coupled via an electrical circuit to the source of light, the acoustic transducer being powered by acoustic energy providable by an external acoustic energy source to effect current flow to the source of light; (b) implanting the miniature light source at the internal treatment site of a subject in need thereof; and (c) powering the acoustic transducer via the external acoustic energy source, thereby providing the light of the desired wavelength, several discrete wavelengths or waveband to the internal treatment site to effect the photodynamic therapy.

According to still an additional aspect of the present invention there is provided a miniature light source for providing light to an internal treatment site to effect a photodynamic therapy at said site, comprising: (a) a source of light that produces light of a desired wavelength, several discrete wavelengths or waveband when energized by an electrical current; (b) a rechargeable energy storage device operably coupled via an electrical circuit to said source of light; (c) an acoustic transducer coupled to said rechargeable energy storage device, said acoustic transducer being activatable upon acoustic signal by an external acoustic energy source for recharging said rechargeable energy storage device.

According to a further aspect of the present invention there is provided a system for providing light of a desired wavelength, several discrete wavelengths or waveband to a treatment site disposed internally within a patient's body, to effect a photodynamic therapy of the treatment site, comprising: (a) a miniature light source which comprises: (i) a source of light that produces light of a desired wavelength, several discrete wavelengths or waveband when energized by an electrical current; (ii) a rechargeable energy storage device operably coupled via an electrical circuit to said source of light; (iii) an acoustic transducer coupled to said rechargeable energy storage device, said acoustic transducer being activatable upon acoustic signal by an external acoustic energy source for recharging said rechargeable energy storage device; and (b) said external acoustic energy source for recharging said rechargeable energy storage device.

According to yet a further aspect of the present invention there is provided a method for providing light of a desired wavelength, several discrete wavelengths or waveband to an internal treatment site to effect a photodynamic therapy, comprising: (a) providing a miniature light source which comprises: (i) a source of light that produces light of a desired wavelength, several discrete wavelengths or waveband when energized by an electrical current; (ii) a rechargeable energy storage device operably coupled via an electrical circuit to said source of light; (iii) an acoustic transducer coupled to said rechargeable energy storage device, said acoustic transducer being activatable upon acoustic signal by an external acoustic energy source for recharging said rechargeable energy storage device; (b) implanting said miniature light source at the internal treatment site of a subject in need thereof; and (c) recharging said rechargeable energy storage device via said acoustic transducer and said external acoustic energy source.

According to further features in preferred embodiments of the invention described below, the method further comprising administering to the subject a therapeutically effective amount of a photodynamic therapy agent.

According to still further features in the described preferred embodiments the miniature light source further comprises a rectifier that is connected to the acoustic transducer, the rectifier converting an alternating current to a direct current. In one embodiment the direct current is supplied to energize the light source. In another embodiment the direct current is used to recharge the rechargeable energy storage device.

According to still further features in the described preferred embodiments the miniature light source further comprises a biocompatible, light transmitting, acoustic energy transmitting, material that encloses the source of light and the acoustic transducer, to form a bead, the bead being thus adapted for insertion into the internal treatment site to effect the photodynamic therapy by providing light to the treatment site.

According to still further features in the described preferred embodiments the bead is generally spherical and less than 5 mm in diameter. According to still further features in the described preferred embodiments the bead is generally semi-spherical, less than 5 mm in diameter and less than 2.5 mm in height.

According to still further features in the described preferred embodiments the source of light comprises a LED.

According to still further features in the described preferred embodiments the source of light comprises a fluorescent light source.

According to still further features in the described preferred embodiments the source of light comprises an electroluminescent source.

According to still further features in the described preferred embodiments the source of light comprises a LD.

According to still further features in the described preferred embodiments the miniature light source further comprises a light diffuser disposed to diffuse the light emitted by the source of light.

According to still further features in the described preferred embodiments the light diffuser is a lens disposed to diffuse the light emitted by the source of light.

According to still further features in the described preferred embodiments the rechargeable energy storage device is selected from the group consisting of a rechargeable battery and a capacitor.

According to still further features in the described preferred embodiments, implanting the miniature light source at the internal treatment site is effected by injection or catheterization.

According to still further features in the described preferred embodiments the injecting comprises inserting a distal end of a needle that is connected to a syringe containing the miniature light source into the treatment site, and forcing the bead from the syringe into the treatment site through the needle.

According to still further features in the described preferred embodiments activating the acoustic transducer via the external acoustic energy source is effected by placing the external acoustic energy source against a body portion of a treated subject and activating the external acoustic energy source.

According to still further features in the described preferred embodiments, the method further comprising injecting a plurality of miniature light sources into the treatment site at spaced-apart locations.

According to still further features in the described preferred embodiments the acoustic transducer comprises: a cell member having a cavity; a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and a first electrode attached to the external surface and a second electrode attached to the internal surface.

According to still further features in the described preferred embodiments the acoustic transducer comprises a transducer element adapted for converting acoustic wave energy transmitted through an external fluid medium into electric energy, the transducer element comprising: a cell member having a cavity; a substantially flexible piezoelectric layer peripherally attached to the cell member so as to isolate the cavity from the external fluid medium, the cavity containing gas and having a substantially lower acoustic impedance than the external fluid medium, a central portion of the piezoelectric layer not rigidly affixed with respect to the cavity, the piezoelectric layer having an external surface and an internal surface, the piezoelectric layer featuring such dimensions so as to enable fluctuations thereof in-and-out of the cavity at its resonance frequency upon impinging of an acoustic signal transmitted through the external fluid medium, the resonance frequency determined by the physical dimensions of the cavity and the piezoelectric layer wherein the wavelength of the acoustic signal is substantially larger than the dimensions; and a first electrode attached to the external surface and a second electrode attached to the internal surface.

According to still further features in the described preferred embodiments the cavity is etched or drilled into a substrate.

According to still further features in the described preferred embodiments the substrate includes an electrically insulating layer and an electrically conducting layer.

According to still further features in the described preferred embodiments the first electrode is integrally made with a substantially thin electrically conducting layer disposed on the substrate.

According to still further features in the described preferred embodiments the substantially thin electrically conducting layer is connected to the substrate by means of a sealing connection.

According to still further features in the described preferred embodiments the electrically insulating layer is made of silicon.

According to still further features in the described preferred embodiments the electrically insulating layer is made of a polymeric material.

According to still further features in the described preferred embodiments the piezoelectric layer is made of PVDF.

According to still further features in the described preferred embodiments the cavity is circular in cross section.

According to still further features in the described preferred embodiments the cavity is elliptical in cross section.

According to still further features in the described preferred embodiments the cavity is hexagonal in cross section.

According to still further features in the described preferred embodiments the substrate includes a plurality of cell members.

According to still further features in the described preferred embodiments at least one of the first and second electrodes is specifically shaped so as to provide a maximal electrical output.

According to still further features in the described preferred embodiments at least one of the electrodes features first and second electrode portions interconnected by a connecting member.

According to still further features in the described preferred embodiments the gas is of substantially low pressure.

According to still further features in the described preferred embodiments the miniature light source is preprogrammed to shut off a predetermined time period following its activation.

According to still further features in the described preferred embodiments the miniature light source shuts off following a reception of an external shut off signal.

The present invention successfully addresses the shortcomings of the presently known configurations by providing an intrabody implantable light sources which, are powered and/or controlled by acoustic energy or signals, respectively, and hence, can be miniature and, at the same time, be implanted deep within the body.

Implementation of the device, method and system of the present invention involves performing or completing selected tasks or steps manually, automatically, or a combination thereof. Moreover, according to actual instrumentation and equipment of preferred embodiments of the device, method and system of the present invention, several selected steps could be implemented by hardware or by software on any operating system. For example, as hardware, selected steps of the invention could be implemented as a chip or a circuit. As software, selected steps of the invention could be implemented as a plurality of software instructions being executed by a computer using any suitable operating system. In any case, selected steps of the device, method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2a is a cross section of a prior art transducer element used in the miniature light source, system and method according to the present invention taken along line C—C in FIG. 1–i a;

FIG. 2b is a cross section of a prior art transducer element used in the miniature light source, system and method according to the present invention taken along line D—D in FIG. 1a;

FIG. 2c is a cross section of a prior art transducer element used in the miniature light source, system and method according to the present invention taken along line E—E in FIG. 1a;

FIG. 2d is a cross section of a prior art transducer element used in the miniature light source, system and method according to the present invention taken along line F—F in FIG. 1a;

FIG. 2e is a cross section of a prior art transducer element used in the miniature light source, system and method according to the present invention taken along line G—G in FIG. 1a;

FIG. 7a is an isometric view of a miniature light source according to the present invention having a single acoustic transducer and a single enlarged LED;

FIG. 7b is a cross sectional view of a miniature light source according to the present invention having a single acoustic transducer encapsulated within a fluid filled casing and a single enlarged LED;

FIG. 8 is a perspective view of a miniature light source according to the present invention having a plurality of acoustic transducers and a plurality of smaller LEDs and having a semispherical construction;

FIG. 9 is a perspective view of a miniature light source according to the present invention having a plurality of acoustic transducers and a plurality of smaller LEDs and having a spherical construction;

FIGS. 15a–b are outline depictions of miniature light sources according to the present invention having spherical and semispherical constructions;

FIG. 16 is a cross sectional view of a light diffuser used in context of the present invention;

FIG. 17 is a schematic depiction of a system according to the present invention.

DESCRIPTION OF THE PREFERRED EMBODIMENTS

Figure 1A:
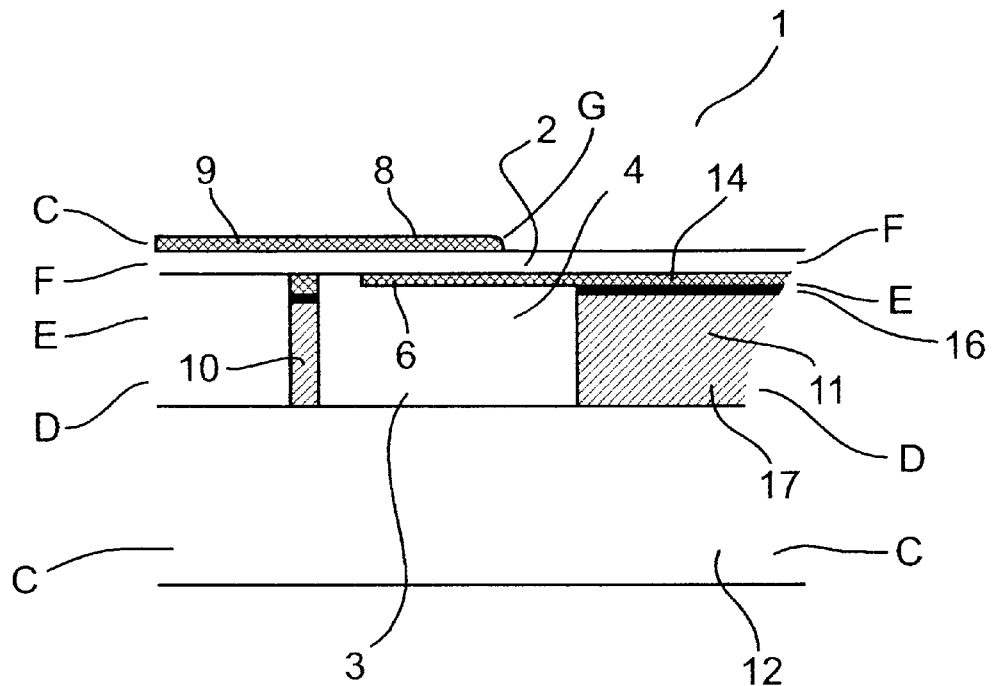
FIG. 1a is a longitudinal section of a transducer element used in the miniature light source, system and method according to the present invention taken along lines A—A in FIGS. 2a–2e.

The present invention is of a miniature light source, system incorporating same and method exploiting same for effecting photodynamic therapy. Specifically, the present invention can be used to effect long lasting intrabody PDT in depths unprecedented by prior art designs using minimal invasive procedures.

The principles and operation of a light source, system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

U.S. Pat. No. 6,140,740 to Porat et al., the teachings of which are incorporated herein by reference, disclose a miniature acoustic transducer characterized by high acoustic to electrical conversion efficiency.

FIGS. 1a–6 which are described in detail hereinbelow provide details concerning the construction and operation of the miniature acoustic transducer of U.S. Pat. No. 6,140,740.

Referring now to the drawings, FIGS. 1a, 1b and 2a–2e illustrate a preferred embodiment of a transducer element used in a miniature light source according to the present invention. As shown in the figures, the transducer element 1 includes at least one cell member 3 including a cavity 4 etched or drilled into a substrate and covered by a substantially flexible piezoelectric layer 2. Attached to piezoelectric layer 2 are an upper electrode 8 and a lower electrode 6, the electrodes serve for connection to an electrical (e.g., electronic) circuit.

The substrate is preferably made of an electrical conducting layer 11 disposed on an electrically insulating layer 12, such that cavity 4 is etched or drilled substantially through the thickness of electrically conducting layer 11.

Electrically conducting layer 11 is preferably made of copper and insulating layer 12 is preferably made of a polymer such as polyimide. Conventional copper-plated polymer laminate such as Kapton sheets may be used for the production of transducer element 1. Commercially available laminates such as Novaclad™ may be used. Alternatively, the substrate may include a silicon layer, or any other suitable material. Alternatively, layer 11 is made of a non-conductive material such as Pyralin™.

Preferably, cavity 4 is etched or drilled into the substrate by using conventional printed-circuit photolithography methods. Alternatively, cavity 4 may be etched or drilled into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m.

Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, a miniature transducer element is provided whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

The transducer described herein is omnidirectional, i.e., insensitive to the direction of the impinging acoustic rays, thereby substantially simplifying the transducer's operation.

According to a specific embodiment, cavity 4 features a circular or hexagonal shape with radius of about 200–800 $\mu$m. Electrically conducting layer 11 preferably has a thickness of about 0.2–15 $\mu$m. Cell member 3 is preferably etched or drilled completely through the thickness of electrically conducting layer 11. Electrically insulating layer 12 preferably features a thickness of about 50 $\mu$m. The precise dimensions of the various elements of a transducer element described herein may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
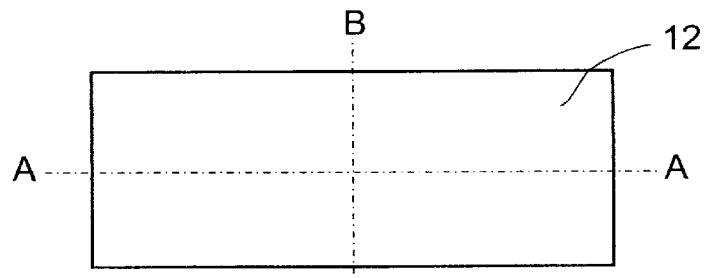
Figure 2B:
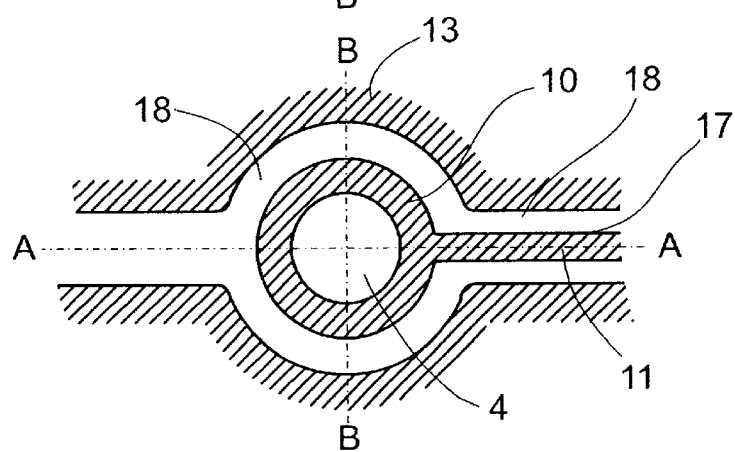

As shown in FIG. 2b, an insulating chamber 18 is etched or drilled into the substrate, preferably through the thickness of conducting layer 11, so as to insulate the transducer element from other portions of the substrate which may include other electrical components such as other transducer elements etched or drilled into the substrate. According to a specific embodiment, the width of insulating chamber 18 is about 100 $\mu$m. As shown, insulating chamber 18 is etched or drilled into the substrate so as to form a wall 10 of a predetermined thickness enclosing cavity 4, and a conducting line 17 integrally made with wall 10 for connecting the transducer element to another electronic component preferably etched or drilled into the same substrate, or to an external electronic circuit.

Figure 1B:
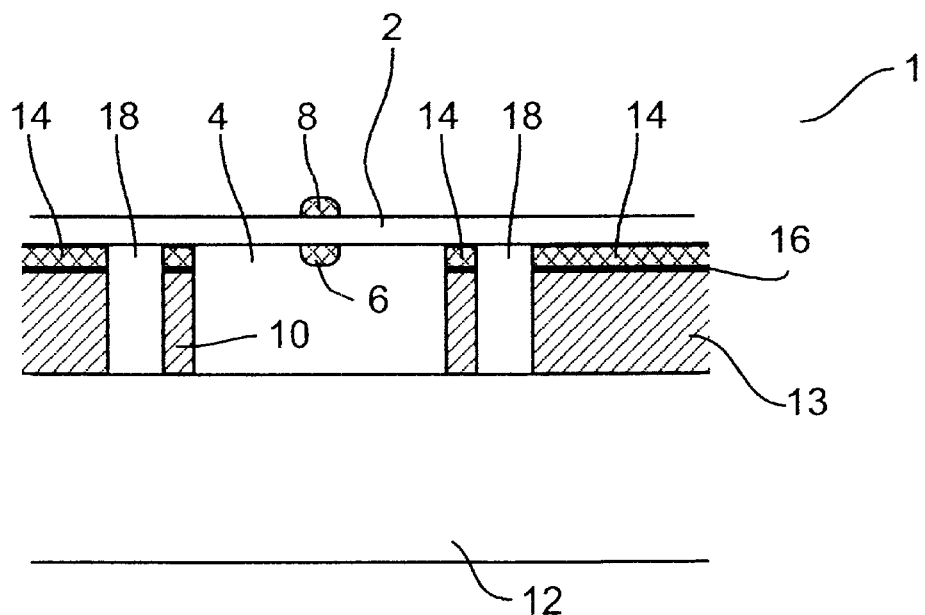
FIG. 1b is a longitudinal section of a prior art transducer element used in the miniature light source, system and method according to the present invention taken along lines B—B in FIGS. 2a–2e.
Figure 2C:
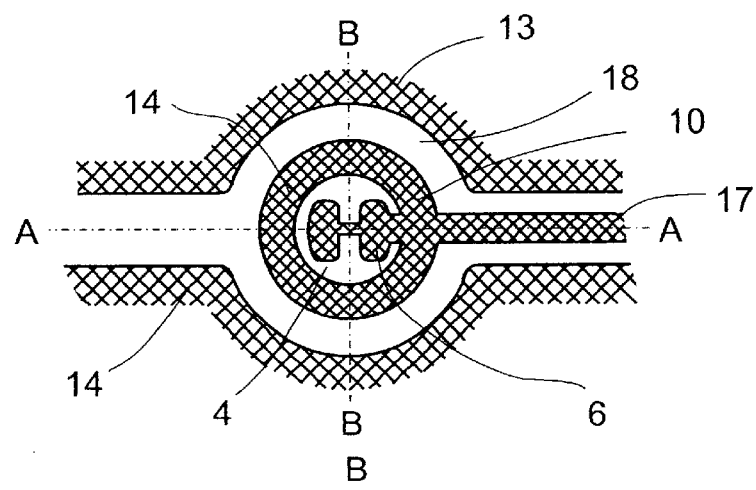
Figure 2D:
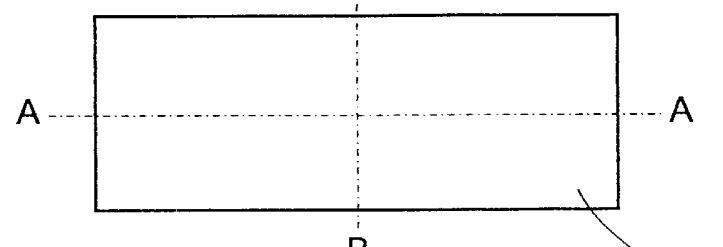
Figure 2E:
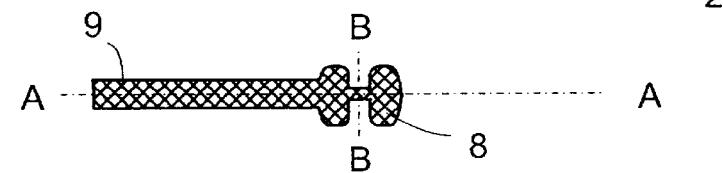

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1a, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2c, electrically conducting layer 14 covers the various portions of conducting layer 11, including wall 10 and conducting line 17. The portion of conducting layer 14 covering conducting line 17 is for connection to an electronic component such as a neighboring cell. Electrodes 6 and 8 are preferably specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$ wherein $\rho$ is the density of layer 2 and $\Omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r, \varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \; L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega \rho_W a$$

wherein:

$\Psi(r,\phi)$ is time-dependent and represents the displacement of a selected point located on circular layer 2, the specific location of which is given by radius r and angle $\phi$;

J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = e_{31}\left(\frac{\partial \Psi}{\partial x}\right)^2 + e_{32}\left(\frac{\partial \Psi}{\partial y}\right)^2$$

wherein:

$Q(r,\phi,t)$ represents the charge density at a selected point located on circular layer 2, the specific location of which is given by radius r and angle $\phi$;

x is the stretch direction of piezoelectric layer 2; y is the transverse direction (the direction perpendicular to the stretch direction) of layer 2;

$e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer.

$\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\Psi, t)$ over the entire area S of the electrode:

$$Q = \int_S Q(r, \varphi, t)\,d\vec{x}$$

The capacitance C of piezoelectric layer 2 is given by:

$$C = \frac{\varepsilon}{2h}\int_S d\vec{x},$$

wherein $\in$ is the dielectric constant of piezoelectric layer 2; and $2h$ is the thickness of piezoelectric layer 2.

Accordingly, the voltage, current and power responses of piezoelectric layer 2 are evaluated as follows:

$$V = \frac{2h\int_S Q(r, \varphi, t)\,d\vec{x}}{\varepsilon \int_S d\vec{x}}, \; I = 2i\omega \int_S Q(r, \varphi, t)\,d\vec{x},$$

$$W = \frac{4ih\left[\int_S Q(r, \varphi, t)\,d\vec{x}\right]^2}{\varepsilon \int_S d\vec{x}}$$

The DC components of Q are usually removed prior to the evaluation, since the DC currents are usually filtered out. The values of Q given above represent peak values of the AC components of Q, and should be modified accordingly so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
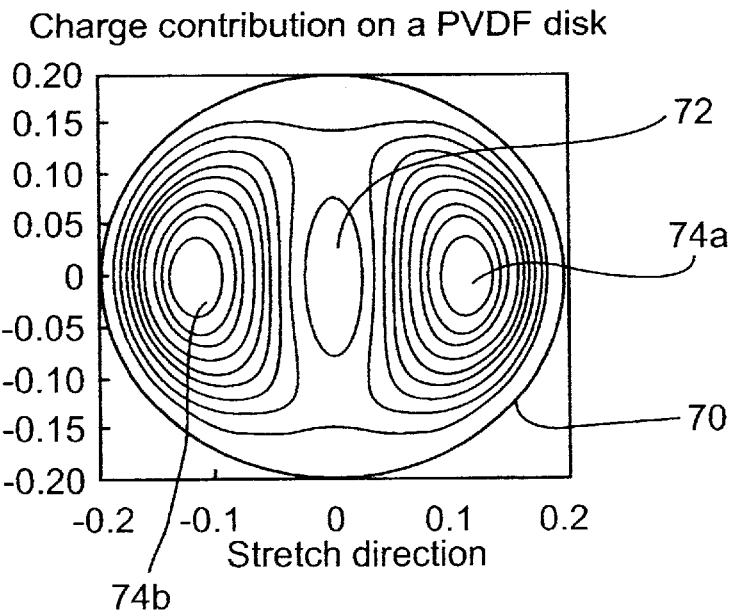
FIG. 3 shows the distribution of charge density across a piezoelectric layer of a prior art transducer element used in the miniature light source, system and method of the present invention, resulting from the application of a constant pressure over the entire surface of the layer.
Figure 4A:
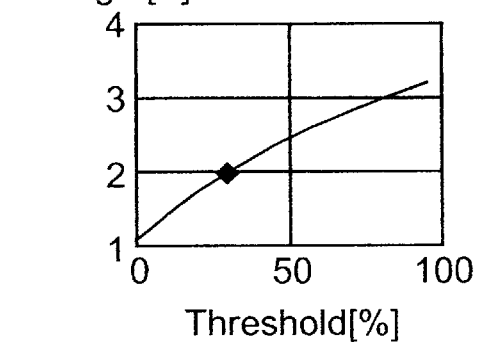
FIG. 4 shows the results of optimization performed for the power response of a prior art transducer used in the miniature light source, system and method according to the present invention.
Figure 4C:
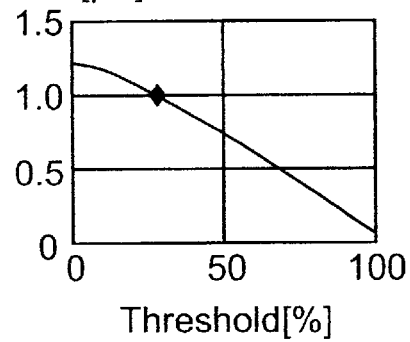
Figure 4B:
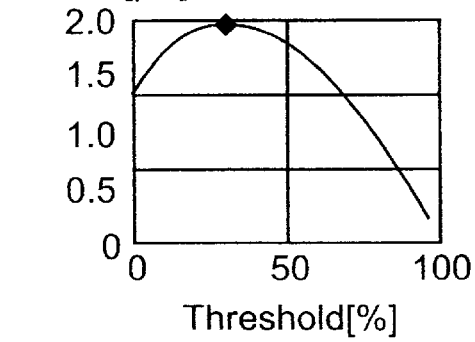
Figure 4D:
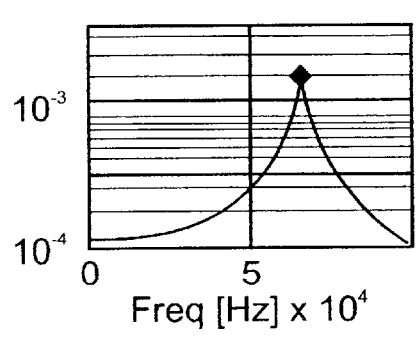

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74*a* and 74*b* located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 4 shows the results of an optimization performed for the power response of a transducer having a layer 2 of a predetermined area. As shown in the figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the figure, the deflection of layer 2 is maximal when applying an acoustic signal at the resonant frequency of layer 2 (graph d).

Figure 5:
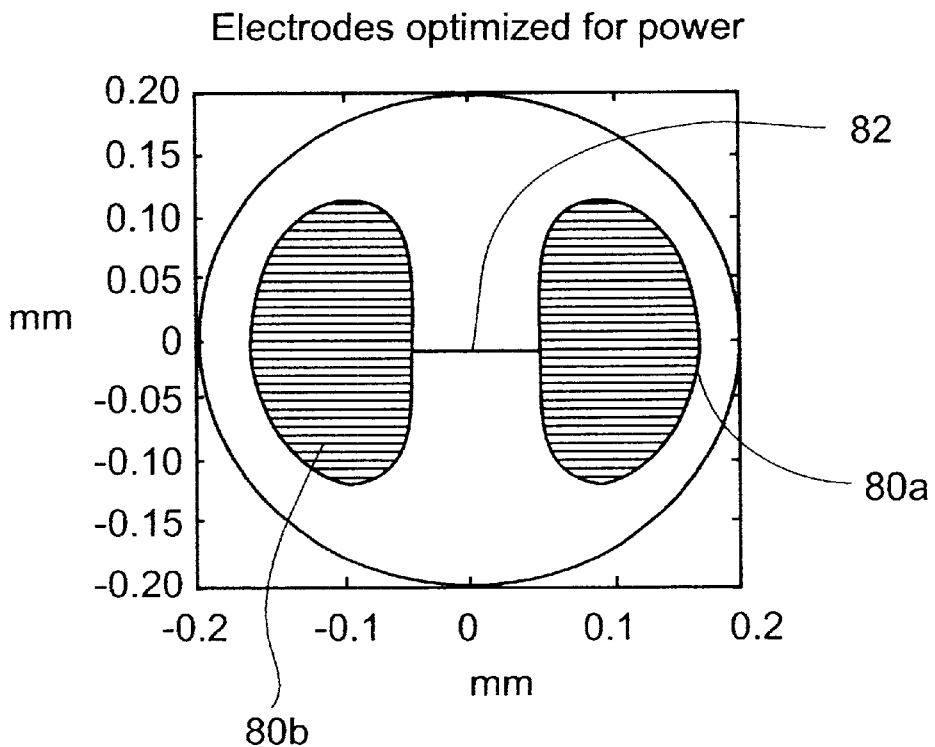
FIG. 5 shows a preferred electrode shape for maximizing the power response of a prior art transducer element used in the miniature light source, system and method according to the present invention.

A preferred electrode shape for maximizing the power response of the transducer is shown in FIG. 5, wherein the electrode includes two electrode portions 80*a* and 80*b* substantially covering the maximal charge density portions of layer 2, the electrode portions being interconnected by means of a connecting member 82 having a minimal area. Preferably, portions 80*a* and 80*b* cover the portions of layer 2 which yield at least a selected threshold (e.g. 30%) of the maximal charge density.

Any other parameter may be optimized so as to determine the shape of electrodes 6 and 8. In addition, one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
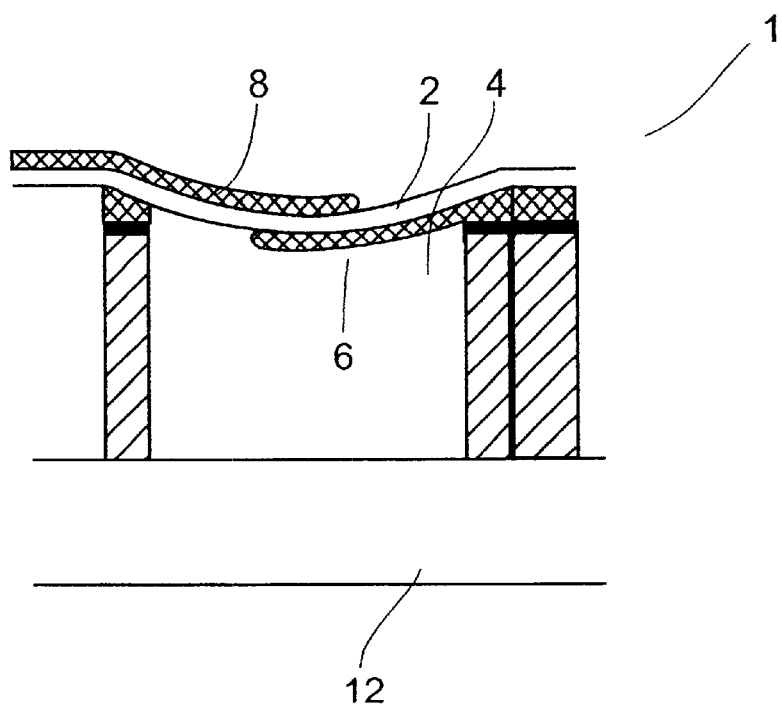
FIG. 6 is a longitudinal section of another embodiment of a prior art transducer element used in the miniature light source, system and method according to the present invention, which embodiment is adapted for further miniaturization.

Referring now to FIG. 6, according to another embodiment of the present invention chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{DC}$ the displacement resulting from P.

Accordingly, the strain along the x direction includes three terms as follows:

$$S_{xx} = \left(\frac{\partial \Psi}{\partial x}\right)^2 = P_0^2\left(\frac{\partial \Psi_{DC}}{\partial x}\right)^2 + P^2\left(\frac{\partial \Psi_{AC}}{\partial x}\right)^2 \cos^2\omega t + 2P_0 P \frac{\partial \Psi_{DC}}{\partial x}\frac{\partial \Psi_{AC}}{\partial x}\cos\omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment of the present invention makes it possible to increase the charge output of layer 2 for a given displacement, thereby increasing the voltage, current and power responses of the transducer without having to increase the acoustic pressure P. Further, such embodiment enables to further miniaturize the transducer since the same electrical response may obtain for smaller acoustic deflections. Such embodiment is substantially more robust mechanically and therefore more durable than the embodiment shown in FIGS. 1*a* and 1*b*. Such further miniaturization of the transducer enables to use higher resonance frequencies relative to the embodiment shown in FIGS. 1*a* and 1*b*.

Preferably, a transducer element 1 is fabricated by using technologies which are in wide use in the microelectronics industry so as to allow integration thereof with other conventional electronic components. When the transducer element includes a substrate such as Copper-polymer laminate or silicon, a variety of conventional electronic components may be fabricated onto the same substrate.

According to the present invention, a plurality of cavities 4 may be etched or drilled into a single substrate 12 and covered by a single piezoelectric layer 2 so as to provide a transducer element including a matrix of transducing cells members 3, thereby providing a larger energy collecting area of predetermined dimensions while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Further, piezoelectric layer 2 may be completely depolarized and then repolarized at specific regions thereof so as to provide a predetermined polarity to each of the transducing cell members 3. Such configuration enables to reduce the complexity of interconnections between the cell members 3.

The human body is transparent to ultrasonic waves up to a high frequency (~10 MHz).

Referring now to FIGS. 7–11, according to one aspect of the present invention there is provided a miniature light source 100 for providing light to an internal treatment site to effect a photodynamic therapy at the site. Light source 100 comprises a source of light 102 that produces light of a desired wavelength, several discrete wavelengths or waveband when energized by an electrical current. Light source 100 according to the present invention further comprises an acoustic transducer 104, which is operably coupled via an electrical circuit (see FIG. 11) to source of light 102. Acoustic transducer 104 is powered by acoustic energy providable by an external acoustic energy source (shown in FIG. 17 as 310) to effect current flow to source of light 102.

Acoustic transducer 104 preferably comprises a transducer element as described and exemplified hereinabove with respect to FIGS. 1a–6, which is adapted for converting acoustic wave energy transmitted through an external fluid medium into electric energy. Hence, the transducer element comprises a cell member having a cavity; a substantially flexible piezoelectric layer peripherally attached to the cell member, so as to isolate the cavity from the external fluid medium, the cavity containing gas and having a substantially lower acoustic impedance than the external fluid medium, a central portion of the piezoelectric layer not rigidly affixed with respect to the cavity, the piezoelectric layer having an external surface and an internal surface, the piezoelectric layer featuring such dimensions so as to enable fluctuations thereof in-and-out of the cavity at its resonance frequency upon impinging of an acoustic signal transmitted through the external fluid medium, the resonance frequency determined by the physical dimensions of the cavity and the piezoelectric layer wherein the wavelength of the acoustic signal is substantially larger than the dimensions. The transducer element further comprises a first electrode attached to the external surface and a second electrode attached to the internal surface.

The following are preferred features of the transducer element which are described in greater detail in context of FIGS. 1a–6, above. Preferably, the cavity is etched or drilled into a substrate. Still preferably, the substrate includes an electrically insulating layer and an electrically conducting layer. Yet preferably, the first electrode is integrally made with a substantially thin electrically conducting layer disposed on the substrate. Preferably, the substantially thin electrically conducting layer is connected to the substrate by means of a sealing connection. Preferably, the electrically insulating layer is made of silicon. Preferably, the electrically insulating layer is made of a polymeric material. Preferably, the sealing connection is made of indium. Preferably, the piezoelectric layer is made of PVDF. Preferably, the cavity is circular in cross section. Preferably, the cavity is elliptical in cross section. Preferably, the cavity is hexagonal in cross section. Preferably, the substrate includes a plurality of cell members. Preferably, at least one of the first and second electrodes is specifically shaped so as to provide a maximal electrical output. Preferably, at least one of the electrodes features first and second electrode portions interconnected by a connecting member. Preferably, the gas is of substantially low pressure.

Figure 10:
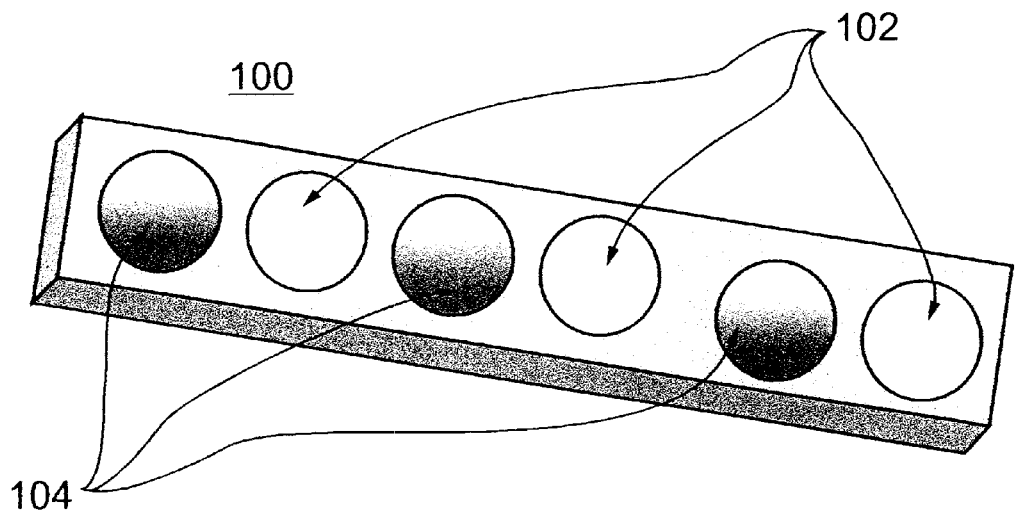
FIG. 10 is a schematic depiction of a miniature light source according to the present invention having a plurality of acoustic transducers and a plurality of LEDs connected thereto via a current rectifier.
Figure 11A:
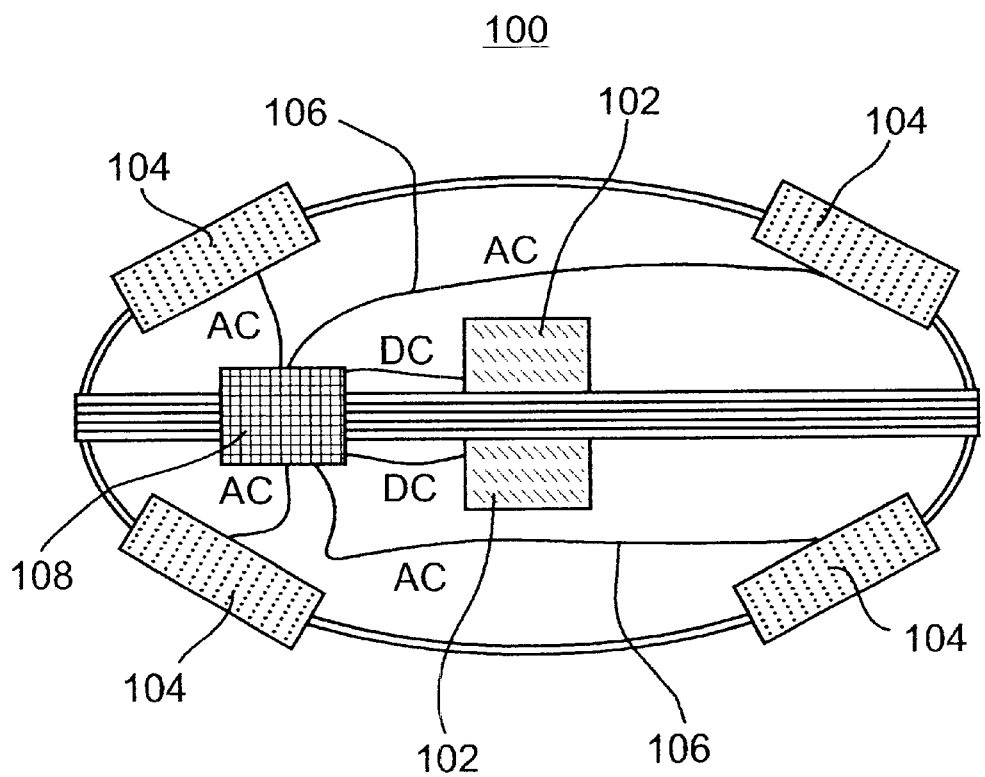
FIG. 11a is perspective view of a miniature light source according to the present invention having a plurality of acoustic transducers and a plurality of LEDs, the miniature light source is shaped as a bar.
Figure 11B:
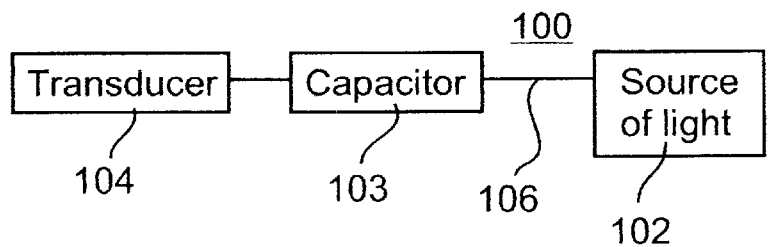
FIG. 11b is a schematic diagram illustrating a miniature light source according to the present invention having a capacitor and which is inherently a pulsating light source.

In the configuration of FIGS. 7a–7b, a single acoustic transducer 104 and a single source of light 102 are shown. On the other hand, in the configurations shown in FIGS. 8–11, several acoustic transducers 104 couples to several source of lights 102 are shown. In FIG. 11a a rectifier 108 that is connected to acoustic transducers 104 serves for converting an alternating current, AC (e.g., about 40 khZ), to a direct current, DC, which is supplied to energize light sources 102 via circuitry 106. Rectifier 112 can be a diode bridge or half bridge. It will be appreciated that the diodes used for the rectifier can be discrete, integrated on a chip, polymer or the LEDs themselves can serve as diodes in the rectifier. In FIGS. 7a and 8 the outline of miniature light source 100 is semispherical, in FIG. 9 it is spherical, whereas in FIG. 11 it is bar-like.

As shown in FIG. 11a, according to a preferred embodiment of this aspect of the present invention, miniature light source 100, further comprising a capacitor 103 in electrical circuit 106. Capacitor 103 is chargeable by the acoustic transducer and dischargeable so as to effect the current flow to source of light 102.

Figure 12:
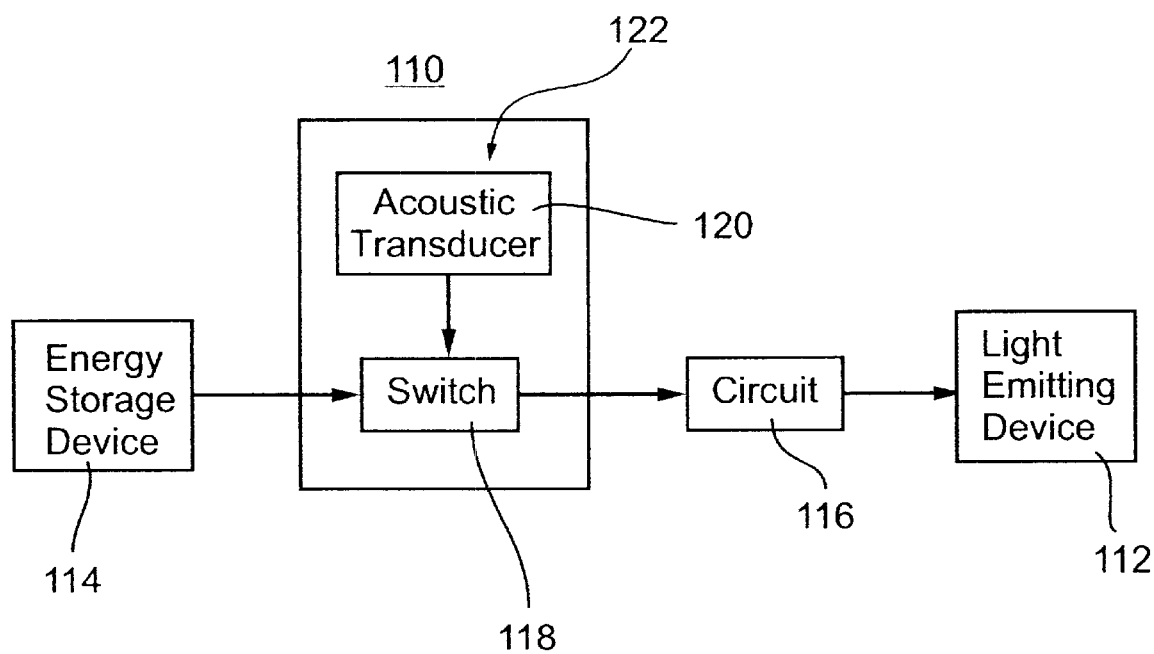
FIG. 12 is a schematic diagram illustrating an acoustic switch utilizable by the device of the present invention.

Reference is now made to FIG. 12. According to another aspect of the present invention there is provided a miniature light source 110 for providing light to an internal treatment site to effect a photodynamic therapy at the site. The miniature light source 110 according to this aspect of the present invention comprises a source of light 112 that produces light of a desired wavelength, several discrete wavelengths or waveband when energized by an electrical current. Source 110 further comprises an energy storage device 114, such as a battery, e.g., a lithium battery, operably coupled via an electrical circuit 116 to source of light 118. Source 110 further comprises a switch 118 operably coupled to electrical circuit the energy storage device. Source 110 further comprises an acoustic transducer 120 coupled to switch 118. Acoustic transducer 120 is activatable, as indicated by arrow 122, upon acoustic excitation by an external acoustic energy source for closing the switch to allow current flow from energy storage device 114 to source of light 112.

PCT/IL01/00951 and U.S. patent application Ser. No. 09/690,615, the teachings of which are hereby incorporated by reference, teach, in detail, a switch controlled by an acoustic transducer.

Figure 13:
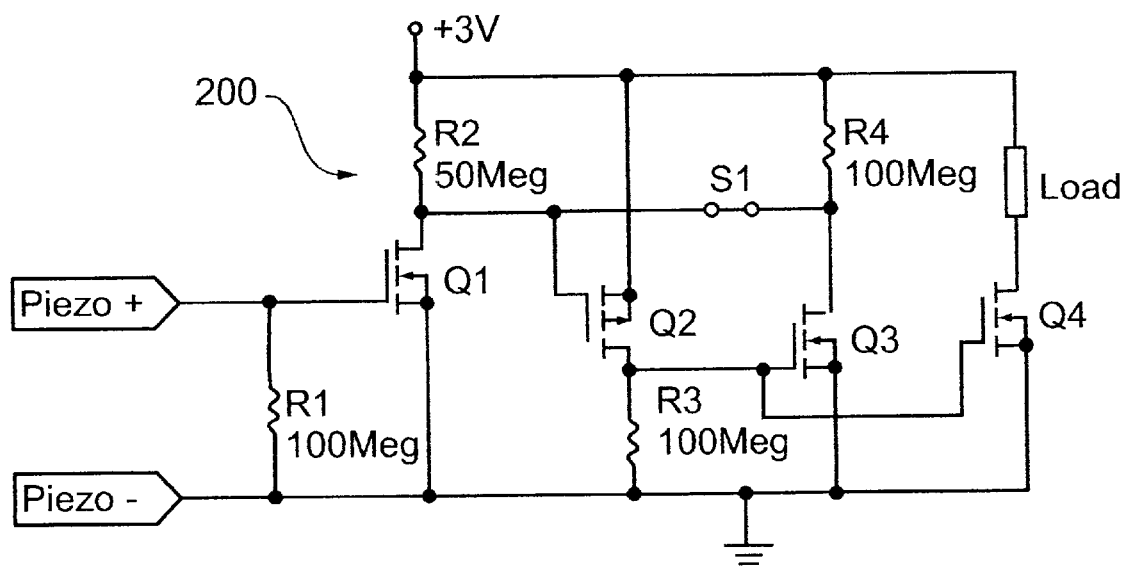
FIG. 13 is schematic diagram illustrating a control circuitry of the acoustic switch illustrated in FIG. 12.

FIG. 13 illustrates an example of circuitry and components employed by an acoustically controlled switch 200 which is utilizable by the light source of the present invention.

Switch 200 includes a piezoelectric transducer, or other acoustic transducer such as the acoustic transducer described hereinabove (not shown, but connectable at locations piezo + and piezo −), a plurality of MOSFET transistors (Q1–Q4) and resistors (R1–R4), and switch S1.

In the switch's "sleep" mode, all of the MOSFET transistors (Q1–Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit.

Therefore, although an energy storage device (not shown, but coupled between the hot post, labeled with an exemplary voltage of +3V, and ground) is connected to switch 200, no current is being drawn therefrom since all of the transistors are quiescent.

When the piezoelectric transducer detects an external acoustic signal, e.g., having a particular frequency such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct through resistor R4 and main switching transistor Q4 begins to conduct through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3 & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open switch 200, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, switch 200 returns to its sleep mode, even if switch S1 is again closed. Switch 200 will only return to its active mode upon receiving a new acoustic activation signal from the piezoelectric transducer.

Preferably the switch is configured such that the switch is closed only when the acoustic transducer receives a first acoustic excitation signal followed by a second acoustic excitation signal, the first and second acoustic excitation signals being separated by a predetermined delay. This feature ensures substantially zero rate of accidental activation of the switch.

Still preferably, the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

Optionally, the acoustic transducer is configured for receiving a first acoustic excitation signal followed by a second acoustic excitation signal, the electrical circuit configured for interpreting the second acoustic excitation signal as one of a predetermined set of commands. Such commands may be, for example, to emit light at a predetermined frequency, to emit light for a predetermined time period, etc.

The use of an acoustic switch as described herein in light source 110 allows the light source to remain in a sleep mode until the electrical circuit is switch on by the acoustic switch. It will be appreciated that an electromagnetic switch would require that the light source will be kept in a standby mode that consumes electrical power and thus shortens the useful operation time of the light source. A magnetic switch, on the other hand, would require a strong extracorporeal magnet, and would suffer from orientation dependence and low reliability.

In a preferred embodiment of this aspect of the invention, the battery employed in light source 110 is a lithium thin film battery (say, LiMn$_2$O$_4$ battery), which has a typically a current density of 100 $\mu$·AHr/(cm$^2$·$\mu$m).

Figure 14:
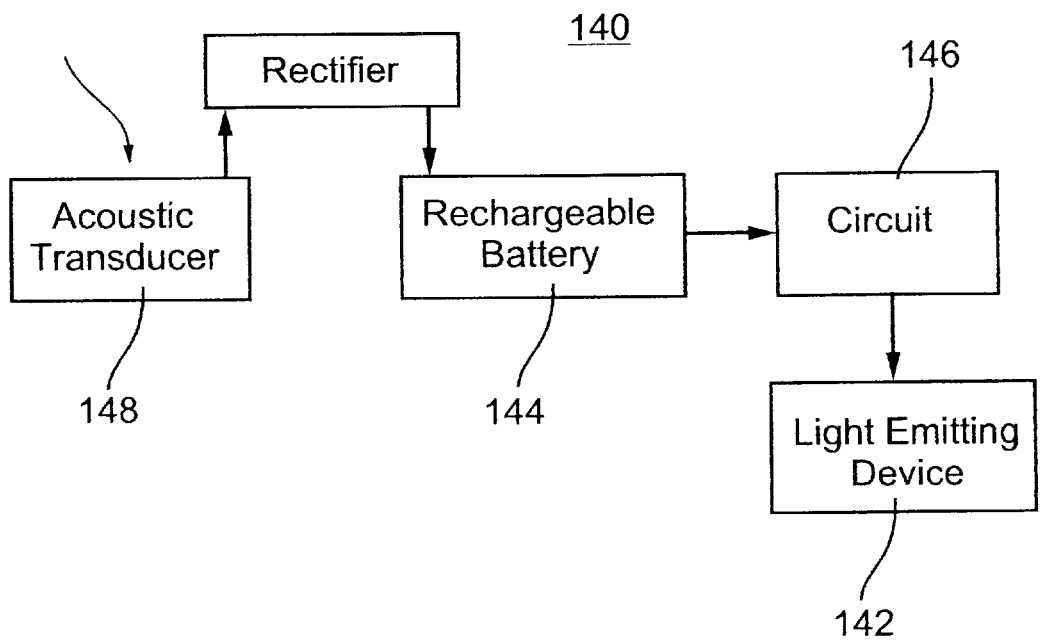
FIG. 14 is a schematic diagram illustrating an a miniature light source according to the present invention in which an acoustic transducer is used to recharge a rechargeable energy storage device.

Thus, for a battery of a surface of 0.3 cm$^2$ having a thickness of 1000 $\mu$m connected to a LED having an operation current of 100$\mu$, the LED operation time is of about 30 hours:

Operation time=100 $\mu$AHr/(cm$^2$·$\mu$m)×1000 $\mu$m×0.3 cm$^2$/100$\mu$=30 hours It will be appreciated that the energy storage device can comprise a rechargeable device, the rechargeable device being rechargeable by a device external to the body. Such recharging can also be effected by acoustic energy transmitted from outside the body to an acoustic transducer operably coupled to the rechargeable device. This configuration is shown schematically in FIG. 14. In this case, a miniature light source 140 includes a source of light 142 that produces light of a desired wavelength, several discrete wavelengths or waveband when energized by an electrical current; a rechargeable energy storage device 144, such as a rechargeable battery or a capacitor, operably coupled via an electrical circuit 146 to source of light 142; and an acoustic transducer 148 coupled to rechargeable energy storage device 144. Acoustic transducer 148 is activatable upon acoustic signal by an external acoustic energy source (See element 310 in FIG. 17) and serves for recharging rechargeable energy storage device 144, so as to allow device 144 to power device 142. The construction and operation of transducer 148 is as described hereinabove with respect to FIGS. 1a–6.

According to preferred embodiments of the present invention, miniature light source 100, 110 or 140 comprises a biocompatible, light transmitting, acoustic energy transmitting, material (identified as 105 in FIG. 7a) that encloses the source of light and the acoustic transducer, to form a bead. The bead is thus adapted for insertion into the internal treatment site to effect the photodynamic therapy by providing light to the treatment site.

In FIG. 7b, acoustic transducer 104 is encapsulated within a case 130 having a thin membrane (say 0.1–100 $\mu$m in thickness) 111 made of a metal or a polymer and filled with an inert material 132, preferably a bio-compatible fluid (e.g., silicon oil), such that the ultrasound waves will be transferred through membrane 111, while acoustic transducer 104 and other components of source 100 are isolated from the body environment.

As shown in FIG. 15a, according to a preferred embodiment, the bead 400a is generally spherical and less than 5, preferably less than 4, more preferably, less than 3 mm in diameter. As shown in FIG. 15b, according to another preferred embodiment, the bead 400b is generally semi-spherical, less than 5 mm in diameter and less than 2.5 mm in height. In preferred embodiments of the invention the entire volume of the miniature light source is less than 5 mm$^3$, preferably, less than 2 mm$^3$. In its bar-like form, as shown in FIG. 10, its cross section is preferably less that 3 mm$^2$, preferably, less than 2 mm$^2$. Such sizes are preferred so as to allow the usage of a minimal invasive procedure, such as injection or catheterization in the implantation of the miniature light source of the present invention in the preferred internal treatment site.

As shown in FIG. 16, in any of the embodiments and configurations of the present invention, the source of light may comprise one or more LEDs, including organic LEDs, for example, LDs, fluorescent light sources and/or electroluminescent sources 500, and the light emitted therefrom may be diffused by a light diffuser 502, such as a diffusing lens, disposed so as to diffuse the light emitted by the source of light.

In any of the embodiments and configurations of the present invention a current and/or voltage sensor that monitors the energy transferred to the implant, the status of the battery (where exists) and the operation of the source of light, e.g., LED, can be used as a means of quality control. The current and/or voltage parameters sensed by the sensor can be transmitted to the external transducer via acoustic telemetry and used for treatment monitoring and optimization.

In some embodiments of the invention, it is advantageous that the light will be emitted from the source of light in pulses, because higher light intensities, for short durations, thus can be used, which increases the effective radius of the miniature light source. This feature is inherent, for example, to the embodiment of the present invention where a capacitor serves as a rechargeable energy storage device or a mediator between the transducer and the source of light. Nevertheless, it will be appreciated by one ordinarily skilled in the art, that suitable circuitry can be used to provide a pulsating effect in all of the other embodiments and configurations offered by the present invention.

According to a preferred embodiment of the invention, the miniature light source, according to any of its embodiments and configurations described herein, is preprogrammed to shut off a predetermined time period following its activation. A circuitry that includes a timer and that can provide this feature is well known in the art.

According to an alternative preferred embodiment of the invention the miniature light source, according to any of its embodiments and configurations described herein shuts off following a reception of an external shut off signal. Such a signal, can, for example, be received by the acoustic transducer which is inherent to all of the embodiments of the miniature light source described herein.

As shown in FIG. 17, according to another aspect of the present invention there is provided a system 300 for providing light of a desired wavelength, several discrete wavelengths or waveband to a treatment site disposed internally within a patient's body, to effect a photodynamic therapy of the treatment site 302. System 300 comprises a miniature light source according to anyone of its embodiments described herein, 100, 110 or 140, and the external acoustic energy source 310, which serves for activating the acoustic transducer in the miniature light source 100, 110 or 140, so as to power the source of light, to control the switch controlling the power supply to the source of light, or to recharge a rechargeable energy storage device which powers the source of light, respectively. External acoustic energy source 310 itself includes a transducer element which converts electrical energy into acoustic energy of predetermined frequency. The transducer element of device 310 can be, yet need not be, similar in construction to the transducer element described in context of FIGS. 1a–6, as there are no physical size constrains in relation thereto.

According to yet another aspect of the present invention there is provided a method for providing light of a desired wavelength, several discrete wavelengths or waveband to an internal treatment site to effect a photodynamic therapy. The method comprises providing a miniature light source according to anyone of its embodiments described herein; implanting the miniature light source at the internal treatment site of a subject in need thereof (as for example shown in FIG. 17); and activating the acoustic transducer via the external acoustic energy source, thereby providing the light of the desired wavelength, several discrete wavelengths or waveband to the internal treatment site to effect the photodynamic therapy.

In practice, a therapeutically effective amount of a photodynamic therapy agent will be administered to the subject and then once an optimal pharmaceutical distribution of the agent is achieved, light of the desired wavelength, several discrete wavelengths or waveband is provided to the internal treatment site to effect photodynamic therapy.

Figure 18A:
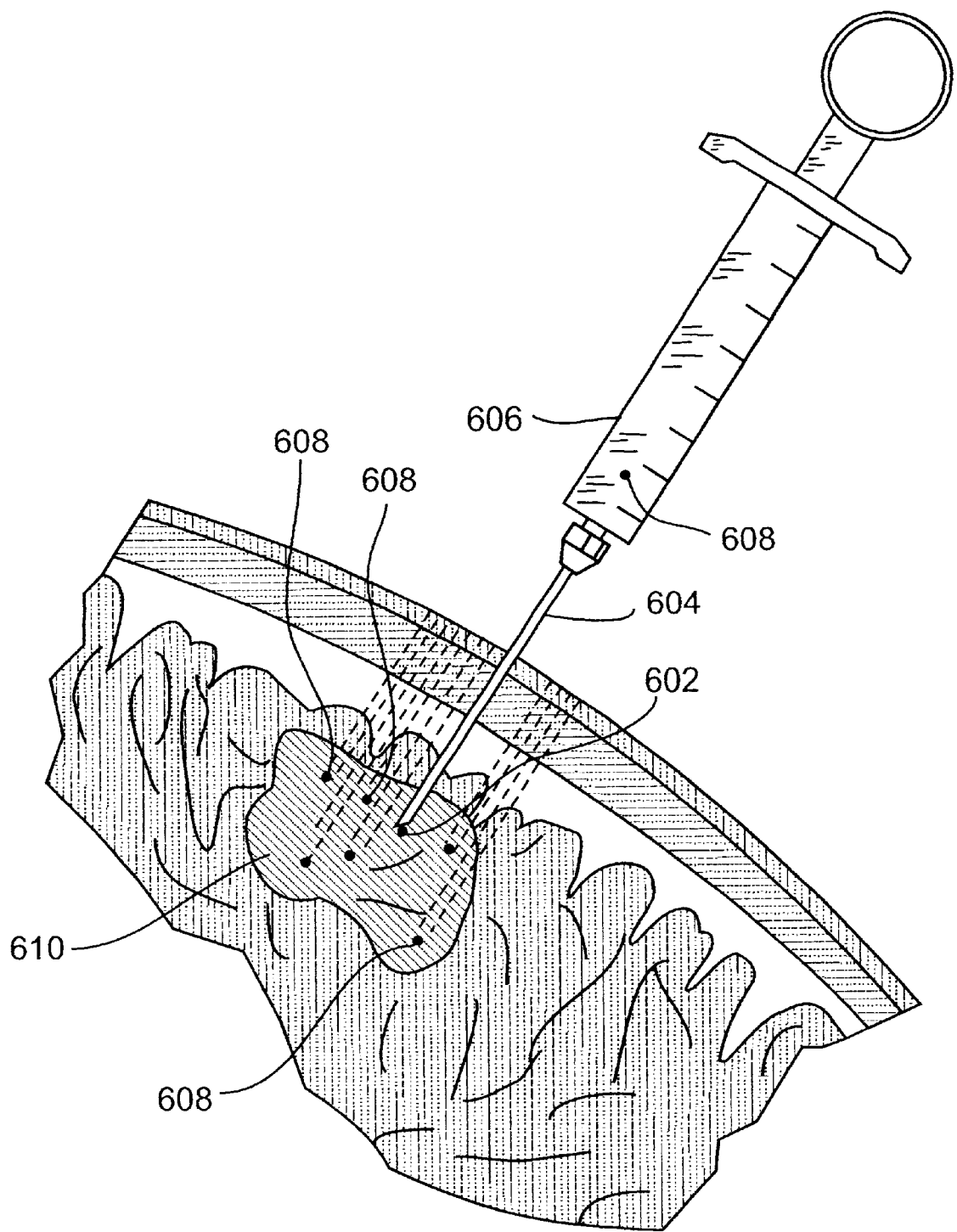
FIGS. 18a–b are illustrations demonstrating the implantation of a miniature light source according to the present invention at an internal treatment site using a syringe needle and a catheter, respectively.
Figure 18B:
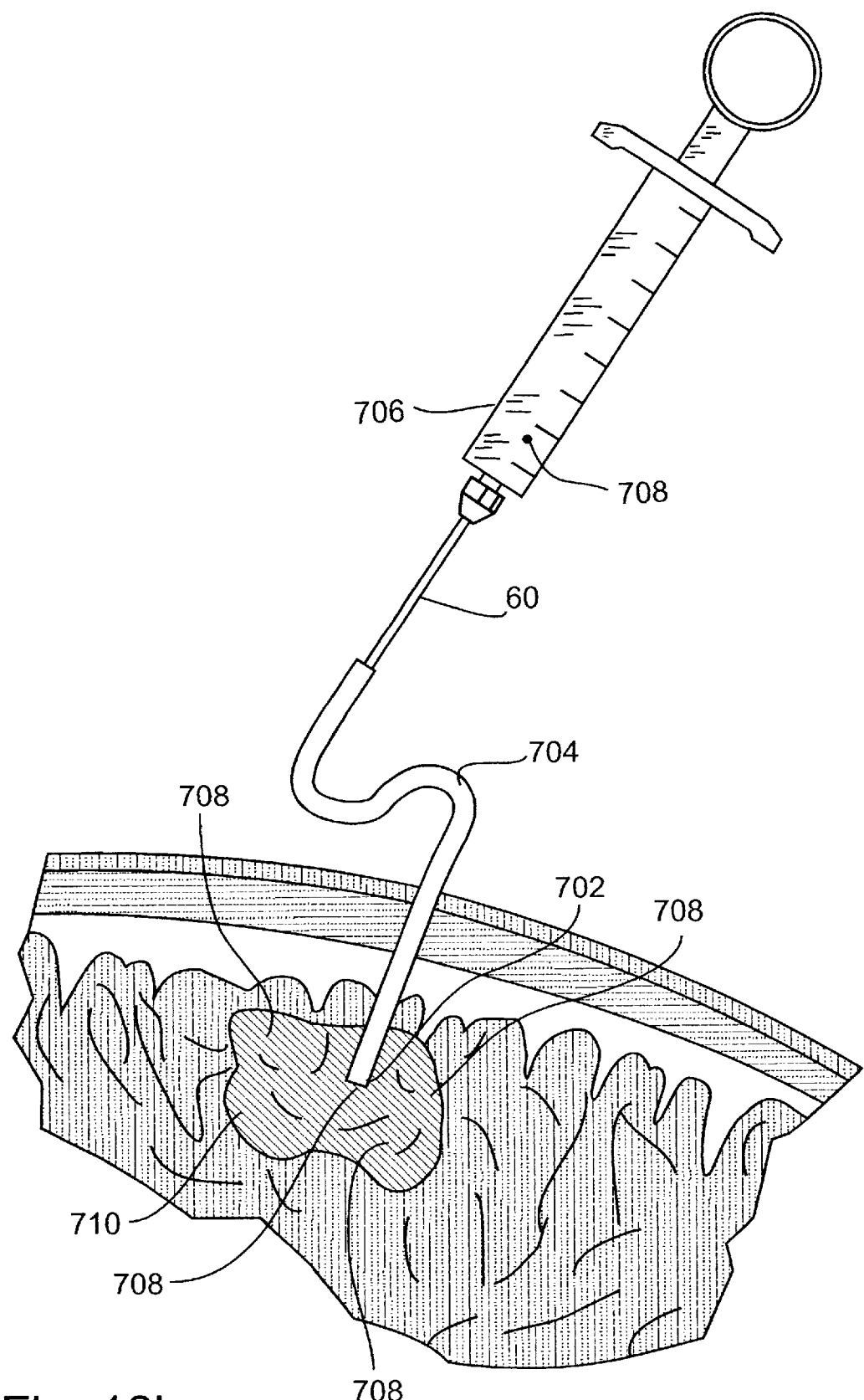

As shown in FIGS. 18a and 18b, implanting the miniature light source at the internal treatment site can be effected, according to the present invention by injection or catheterization, respectively.

As shown in FIG. 18a, injecting may comprise inserting a distal end 602 of a needle 604 that is connected to a syringe 606 containing the miniature light source 608 into the treatment site 610, and forcing the bead 608 from the syringe 606 into the treatment site 610 through the needle 604.

As shown in FIG. 18b, catheterization may comprise inserting a distal end 702 of a catheter 704 that is connected to a syringe 706 containing the miniature light source 708 into the treatment site 710, and forcing the bead 708 from the syringe 706 into the treatment site 710 through the catheter 704.

As is shown in FIGS. 18a–b, preferably a plurality of miniature light sources are placed in the treatment site at spaced-apart locations.

As is shown in FIG. 17, according to a preferred embodiment of the present invention, activating the acoustic transducer via external acoustic energy source 310 is effected by placing external acoustic energy source 310 against a body portion, the chest in the Example of FIG. 17, of the treated subject and activating the external acoustic energy source.

Although in FIGS. 18a–b the treatment site is just underneath the skin, it will be appreciated that the deepest sites in the body such as the bowl, heart, etc., can be treated using the present invention. It will be appreciated that the omnidirectionality of the acoustic transducer employed in context of the present invention, as is further described hereinabove, and the fact that body tissues are transparent to ultrasonic waves up to a high frequency (~10 MHz) ensure that even if the transducer is very small, its direction undefined, and it is implanted deepest in the body, it will still be able to efficiently receive the acoustic energy generated by the external acoustic energy source and well operate.

A wide range of therapeutic benefits may be realized with the apparatus and methods of the present invention, beyond destroying tumors. These benefits include, but are not limited to, the destruction of other abnormal cell types, the destruction of normal tissue for therapeutic ends, selective destruction of pathogenic microorganisms, viruses, and other self-replicating disease agents, treatment of vascular or hematological disorders, reducing or controlling inflammation and the enhancement of normal cellular function, such as wound healing, immunologic response or prevention of restenosis following angioplasty procedures. It is contemplated that the PDT apparatus and method disclosed herein can be applied to providing such therapeutic benefits in both plants and animals.

The miniature light source of the present invention is advantageous in the sense that it is omnidirectional, it is sufficiently small so as to be implanted using a minimal invasive procedure and it well operates regardless of its position in the body. All electromagnetic field based implantable light sources are limited in at least one of these features.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A miniature light source for providing light to an internal treatment site to effect a photodynamic therapy at said site, comprising:
   (a) a source of light that produces light of a desired wavelength, several discrete wavelengths or waveband when energized by an electrical current;
   (b) an energy storage device operably coupled via an electrical circuit to said source of light;
   (c) a switch operably coupled to said electrical circuit and said energy storage device; and
   (d) an acoustic transducer coupled to said switch, said acoustic transducer being activatable upon acoustic excitation by an external acoustic energy source for closing the switch to allow current flow from said energy storage device to said source of light.

2. The miniature light source of claim 1, wherein the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

3. The miniature light source of claim 1, wherein the miniature light source is preprogrammed to shut off a predetermined time period following its activation.

4. The miniature light source of claim 1, wherein the miniature light source shuts off following a reception of an external shut off signal.

5. The miniature light source of claim 1, wherein the acoustic transducer comprises:
   a cell member having a cavity;
   a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
   a first electrode attached to the external surface and a second electrode attached to the internal surface.

6. The miniature light source of claim 1, wherein the energy storage device comprises a battery.

7. The miniature light source of claim 1, designed and operable to generate light pulses.

8. The miniature light source of claim 6, wherein the battery is a lithium battery.

9. The miniature light source of claim 1, wherein the energy storage device comprises a rechargeable device, the rechargeable device being rechargeable by a device external to the body.

10. The miniature light source of claim 1, further comprising a biocompatible, light transmitting, acoustic energy transmitting, material that encloses said source of light, said energy storage device, said electrical circuit, said switch and said acoustic transducer, to form a bead, said bead being thus adapted for insertion into the internal treatment site to effect the photodynamic therapy by providing light to the treatment site.

11. The miniature light source of claim 10, wherein the bead is generally spherical and less than 5 mm in diameter.

12. The miniature light source of claim 10, wherein the bead is generally semi-spherical, less than 5 mm in diameter and less than 2.5 mm in height.

13. The miniature light source of claim 1, wherein said source of light is selected from the group consisting of a LED, a fluorescent light source, an electroluminescent source and a LD.

14. The miniature light source of claim 1, further comprising a light diffuser disposed to diffuse the light emitted by the source of light.

15. The miniature light source of claim 14, wherein said light diffuser is a lens disposed to diffuse the light emitted by the source of light.

16. A system for providing light of a desired wavelength, several discrete wavelengths or waveband to a treatment site disposed internally within a patient's body, to effect a photodynamic therapy of the treatment site, comprising:
   (a) a miniature light source which comprises:
      (i) a source of light that produces light of a desired wavelength, several discrete wavelengths or waveband, several discrete wavelengths or waveband when energized by an electrical current;
      (ii) an energy storage device operably coupled via an electrical circuit to said source of light;
      (iii) a switch operably coupled to said electrical circuit and said energy storage device; and
      (iv) an acoustic transducer coupled to said switch, said acoustic transducer being activatable upon acoustic excitation by an external acoustic energy source for closing the switch to allow current flow from said energy storage device to said source of light; and
   (b) said external acoustic energy source for activating said acoustic transducer.

17. The system claim 16, wherein the miniature light source is preprogrammed to shut off a predetermined time period following its activation.

18. The system of claim 16, wherein the miniature light source shuts off following a reception of an external shut off signal.

19. The system of claim 16, wherein the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

20. The system of claim 16, wherein the acoustic transducer comprises:
   a cell member having a cavity;
   a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
   a first electrode attached to the external surface and a second electrode attached to the internal surface.

21. The system of claim 16, wherein the energy storage device comprises a battery.

22. The system of claim 21, wherein the miniature light source is designed and operable to generate light pulses.

23. The system of claim 21, wherein the battery is a lithium battery.

24. The system of claim 16, wherein the energy storage device comprises a rechargeable device, the rechargeable device being rechargeable by a device external to the body.

25. The system of claim 16, wherein the miniature light source further comprises a biocompatible, light transmitting, acoustic energy transmitting, material that encloses said source of light, said energy storage device, said electrical circuit, said switch and said acoustic transducer, to form a bead, said bead being thus adapted for insertion into the internal treatment site to effect the photodynamic therapy by providing light to the treatment site.

26. The system of claim 25, wherein the bead is generally spherical and less than 5 mm in diameter.

27. The system of claim 25, wherein the bead is generally semi-spherical, less than 5 mm in diameter and less than 2.5 mm in height.

28. The system of claim 16, wherein said source of light is selected from the group consisting of a LED, a fluorescent light source, an electroluminescent source and a LD.

29. The system of claim 16, wherein the miniature light source further comprises a light diffuser disposed to diffuse the light emitted by the source of light.

30. The system of claim 29, wherein said light diffuser is a lens disposed to diffuse the light emitted by the source of light.

31. A method for providing light of a desired wavelength, several discrete wavelengths or waveband to an internal treatment site to effect a photodynamic therapy, comprising:
(a) providing a miniature light source which comprises:
    (i) a source of light that produces light of a desired wavelength, several discrete wavelengths or waveband when energized by an electrical current;
    (ii) an energy storage device operably coupled via an electrical circuit to said source of light;
    (iii) a switch operably coupled to said electrical circuit and said energy storage device; and
    (iv) an acoustic transducer coupled to said switch, said acoustic transducer being activatable upon acoustic excitation by an external acoustic energy source for closing the switch to allow current flow from said energy storage device to said source of light;
(b) implanting said miniature light source at the internal treatment site of a subject in need thereof; and
(c) activating said acoustic transducer via said external acoustic energy source, thereby providing the light of the desired wavelength, several discrete wavelengths or waveband to the internal treatment site to effect the photodynamic therapy.

32. The method of claim 31, wherein the miniature light source is preprogrammed to shut off a predetermined time period following its activation.

33. The method of claim 31, wherein the miniature light source shuts off following a reception of an external shut off signal.

34. The method of claim 31, further comprising administering to the subject a therapeutically effective amount of a photodynamic therapy agent.

35. The method of claim 31, wherein the acoustic transducer is configured for receiving a first acoustic excitation signal and a second acoustic excitation signal, the switch being closed when the first acoustic excitation signal is received by the acoustic transducer, and the switch being opened when the second acoustic excitation signal is received by the acoustic transducer for discontinuing current flow from the energy storage device to the electrical circuit.

36. The method of claim 31, wherein the acoustic transducer comprises:
a cell member having a cavity;
a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
a first electrode attached to the external surface and a second electrode attached to the internal surface.

37. The method of claim 31, wherein the energy storage device comprises a battery.

38. The method of claim 31, wherein the miniature light source is designed and operable to generate light pulses.

39. The method of claim 37, wherein the battery is a lithium battery.

40. The method of claim 31, wherein the energy storage device comprises a rechargeable device, the rechargeable device being rechargeable by a device external to the body.

41. The method of claim 31, wherein the miniature light source further comprises a biocompatible, light transmitting, acoustic energy transmitting, material that encloses said source of light, said energy storage device, said electrical circuit, said switch and said acoustic transducer, to form a bead, said bead being thus adapted for insertion into the internal treatment site to effect the photodynamic therapy by providing light to the treatment site.

42. The method of claim 41, wherein the bead is generally spherical and less than 5 mm in diameter.

43. The method of claim 41, wherein the bead is generally semi-spherical, less than 5 mm in diameter and less than 2.5 mm in height.

44. The method of claim 31, wherein said source of light is selected from the group consisting of a LED, a fluorescent light source, an electroluminescent source and a LD.

45. The method of claim 31, wherein the miniature light source further comprises a light diffuser disposed to diffuse the light emitted by the source of light.

46. The method of claim 45, wherein said light diffuser is a lens disposed to diffuse the light emitted by the source of light.

47. The method of claim 31, wherein implanting said miniature light source at the internal treatment site is effected by injection or catheterization.

48. The method of claim 47, wherein said injecting comprises inserting a distal end of a needle that is connected to a syringe containing the miniature light source into the treatment site, and forcing the bead from the syringe into the treatment site through the needle.

49. The method of claim 31, wherein activating said acoustic transducer via said external acoustic energy source is effected by placing said external acoustic energy source against a body portion of a treated subject and activating said external acoustic energy source.

50. The method of claim 31, further comprising injecting a plurality of miniature light sources into the treatment site at spaced-apart locations.

51. A miniature light source for providing light to an internal treatment site to effect a photodynamic therapy at said site, comprising:
(a) a source of light that produces light of a desired wavelength, several discrete wavelengths or waveband when energized by an electrical current;
(b) an acoustic transducer being operably coupled via an electrical circuit to said source of light, said acoustic transducer being powered by acoustic energy providable by an external acoustic energy source to effect current flow to said source of light.

52. The miniature light source of claim 51, further comprising a capacitor in said electrical circuit, said capacitor being chargeable by said acoustic transducer and dischargeable so as to effect said current flow to said source of light.

53. The miniature light source of claim 51, further comprising a rectifier that is connected to the acoustic transducer, said rectifier converting an alternating current to a direct current, which is supplied to energize the light source.

54. The miniature light source of claim 51, wherein the miniature light source is preprogrammed to shut off a predetermined time period following its activation.

55. The miniature light source of claim 51, wherein the miniature light source shuts off following a reception of an external shut off signal.

56. The miniature light source of claim 51, wherein the acoustic transducer comprises:
a cell member having a cavity;
a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
a first electrode attached to the external surface and a second electrode attached to the internal surface.

57. The miniature light source of claim 51, wherein said acoustic transducer comprises a transducer element adapted for converting acoustic wave energy transmitted through an external fluid medium into electric energy, said transducer element comprising:
a cell member having a cavity;
a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and
a first electrode attached to said external surface and a second electrode attached to said internal surface.

58. The miniature light source of claim 57, wherein said cavity is etched or drilled into a substrate.

59. The miniature light source of claim 58, wherein said substrate includes an electrically insulating layer and an electrically conducting layer.

60. The miniature light source of claim 59, wherein said electrically insulating layer is made of a polymeric material.

61. The miniature light source of claim 57, wherein said piezoelectric layer is made of PVDF.

62. The transducer element of claim 57, wherein said cavity is circular in cross section.

63. The transducer element of claim 57, wherein said cavity is elliptical in cross section.

64. The miniature light source of claim 58, wherein said substrate includes a plurality of cell members.

65. The miniature light source of claim 51, wherein at least one of said first and second electrodes is specifically shaped so as to provide a maximal electrical output.

66. The miniature light source of claim 51, further comprising a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

67. The miniature light source of claim 66, wherein the bead is generally spherical and less than 5 mm in diameter.

68. The miniature light source of claim 66, wherein the bead is generally semi-spherical, less than 5 mm in diameter and less than 2.5 mm in height.

69. The miniature light source of claim 51, wherein said source of light is selected from the group consisting of a LED, a fluorescent light source, an electroluminescent source and a LD.

70. The miniature light source of claim 51, further comprising a light diffuser disposed to diffuse the light emitted by the source of light.

71. The miniature light source of claim 70, wherein said light diffuser is a lens disposed to diffuse the light emitted by the source of light.

72. A system for providing light of a desired wavelength, several discrete wavelengths or waveband to a treatment site disposed internally within a patient's body, to effect a photodynamic therapy of the treatment site, comprising:
(a) a miniature light source which comprises:
(i) a source of light that produces light of a desired wavelength, several discrete wavelengths or waveband when energized by an electrical current; and
(ii) an acoustic transducer being operably coupled via an electrical circuit to said source of light, said acoustic transducer being powered by acoustic energy providable by an external acoustic energy source to effect current flow to said source of light; and
(b) said external acoustic energy source for activating said acoustic transducer.

73. The system of claim 72, wherein said miniature light source further comprises a capacitor in said electrical circuit, said capacitor being chargeable by said acoustic transducer and dischargeable so as to effect said current flow to said source of light.

74. The system of claim 72, wherein said miniature light source further comprises a rectifier that is connected to the acoustic transducer, said rectifier converting an alternating current to a direct current, which is supplied to energize the light source.

75. The system of claim 72, wherein the miniature light source is preprogrammed to shut off a predetermined time period following its activation.

76. The system of claim 72, wherein the miniature light source shuts off following a reception of an external shut off signal.

77. The system of claim 72, wherein the acoustic transducer comprises:
a cell member having a cavity;
a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
a first electrode attached to the external surface and a second electrode attached to the internal surface.

78. The system of claim 72, wherein said acoustic transducer comprises a transducer element adapted for converting acoustic wave energy transmitted through an external fluid medium into electric energy, said transducer element comprising:
a cell member having a cavity;
a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and a first electrode attached to said external surface and a second electrode attached to said internal surface.

79. The system of claim 78, wherein said cavity is etched or drilled into a substrate.

80. The system of claim 79, wherein said substrate includes an electrically insulating layer and an electrically conducting layer.

81. The system of claim 80, wherein said electrically insulating layer is made of a polymeric material.

82. The system of claim 83, wherein a sealing connection is made of indium.

83. The system of claim 78, wherein said piezoelectric layer is made of PVDF.

84. The system of claim 78, wherein said cavity is circular in cross section.

85. The system of claim 78, wherein said cavity is elliptic in cross section.

86. The system of claim 79, wherein said substrate includes a plurality of cell members.

87. The system of claim 78, wherein at least one of said first and second electrodes is specifically shaped so as to provide a maximal electrical output.

88. The system of claim 72, wherein the miniature light source further comprises a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

89. The system of claim 88, wherein the bead is generally spherical and less than 5 mm in diameter.

90. The system of claim 88, wherein the bead is generally semi-spherical, less than 5 mm in diameter and less than 2.5 mm in height.

91. The system of claim 72, wherein said source of light is selected from the group consisting of a LED, a fluorescent light source, an electroluminescent source and a LD.

92. The system of claim 72, wherein the miniature light source further comprises a light diffuser disposed to diffuse the light emitted by the source of light.

93. The system of claim 92, wherein said light diffuser is a lens disposed to diffuse the light emitted by the source of light.

94. A method for providing light of a desired wavelength, several discrete wavelengths or waveband to an internal treatment site to effect a photodynamic therapy, comprising:
(a) providing a miniature light source which comprises:
(i) a source of light that produces light of a desired wavelength, several discrete wavelengths or waveband when energized by an electrical current; and
(ii) an acoustic transducer being operably coupled via an electrical circuit to said source of light, said acoustic transducer being powered by acoustic energy providable by an external acoustic energy source to effect current flow to said source of light;
(b) implanting said miniature light source at the internal treatment site of a subject in need thereof; and
(c) powering said acoustic transducer via said external acoustic energy source, thereby providing the light of the desired wavelength, several discrete wavelengths or waveband to the internal treatment site to effect the photodynamic therapy.

95. The method of claim 94, wherein said miniature light source further comprises a capacitor in said electrical circuit, said capacitor being chargeable by said acoustic transducer and dischargeable so as to effect said current flow to said source of light.

96. The method of claim 94, further comprising administering to the subject a therapeutically effective amount of a photodynamic therapy agent.

97. The method of claim 94, wherein the miniature light source is preprogrammed to shut off a predetermined time period following its activation.

98. The method of claim 94, wherein the miniature light source shuts off following a reception of an external shut off signal.

99. The method of claim 94, wherein said miniature light source further comprises a rectifier that is connected to the acoustic transducer, said rectifier converting an alternating current to a direct current, which is supplied to energize the light source.

100. The method of claim 94, wherein the miniature light source further comprises a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

101. The method of claim 100, wherein the bead is generally spherical and less than 5 mm in diameter.

102. The method of claim 100, wherein the bead is generally semi-spherical, less than 5 mm in diameter and less than 2.5 mm in height.

103. The method of claim 94, wherein said source of light is selected from the group consisting of a LED, a fluorescent light source, an electroluminescent source and a LD.

104. The method of claim 94, wherein the miniature light source further comprises a light diffuser disposed to diffuse the light emitted by the source of light.

105. The method of claim 104, wherein said light diffuser is a lens disposed to diffuse the light emitted by the source of light.

106. The method of claim 94, wherein implanting said miniature light source at the internal treatment site is effected by injection or catheterization.

107. The method of claim 106, wherein said injecting comprises inserting a distal end of a needle that is connected to a syringe containing the miniature light source into the treatment site, and forcing the bead from the syringe into the treatment site through the needle.

108. The method of claim 94, wherein activating said acoustic transducer via said external acoustic energy source is effected by placing said external acoustic energy source against a body portion of a treated subject and activating said external acoustic energy source.

109. The method of claim 94, further comprising injecting a plurality of miniature light sources into the treatment site at spaced-apart locations.

110. The method of claim 94, wherein the acoustic transducer comprises:

a cell member having a cavity;

a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and a first electrode attached to the external surface and a second electrode attached to the internal surface.

111. The method of claim 94, wherein said acoustic transducer comprises a transducer element adapted for converting acoustic wave energy transmitted through an external fluid medium into electric energy, said transducer element comprising:

a cell member having a cavity;

a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and a first electrode attached to said external surface and a second electrode attached to said internal surface.

112. The method of claim 111, wherein said cavity is etched or drilled into a substrate.

113. The method of claim 112, wherein said substrate includes an electrically insulating layer and an electrically conducting layer.

114. The method of claim 113, wherein said electrically insulating layer is made of a polymeric material.

115. The method of claim 111, wherein a sealing connection is made of indium.

116. The method of claim 111, wherein said piezoelectric layer is made of PVDF.

117. The method of claim 111, wherein said cavity is circular in cross section.

118. The method of claim 111, wherein said cavity is elliptic in cross section.

119. The method of claim 112, wherein said substrate includes a plurality of cell members.

120. The method of claim 111, wherein at least one of said first and second electrodes is specifically shaped so as to provide a maximal electrical output.

121. A miniature light source for providing light to an internal treatment site to effect a photodynamic therapy at said site, comprising:

(a) a source of light that produces light of a desired wavelength, several discrete wavelengths or waveband when energized by an electrical current;

(b) a rechargeable energy storage device operably coupled via an electrical circuit to said source of light;

(c) an acoustic transducer coupled to said rechargeable energy storage device, said acoustic transducer being activatable upon acoustic signal by an external acoustic energy source for recharging said rechargeable energy storage device.

122. The system of claim 121, wherein said rechargeable energy storage device is selected from the group consisting of a rechargeable battery and a capacitor.

123. The miniature light source of claim 121, further comprising a rectifier that is connected to the acoustic transducer, said rectifier converting an alternating current to a direct current, which is supplied to said rechargeable energy storage device.

124. The miniature light source of claim 121, wherein the miniature light source is preprogrammed to shut off a predetermined time period following its activation.

125. The miniature light source of claim 121, wherein the miniature light source shuts off following a reception of an external shut off signal.

126. The miniature light source of claim 121, wherein the acoustic transducer comprises:

a cell member having a cavity;

a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and a first electrode attached to the external surface and a second electrode attached to the internal surface.

127. The miniature light source of claim 121, wherein said acoustic transducer comprises a transducer element adapted for converting acoustic wave energy transmitted through an external fluid medium into electric energy, said transducer element comprising:

a cell member having a cavity;

a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and a first electrode attached to said external surface and a second electrode attached to said internal surface.

128. The miniature light source of claim 127, wherein said cavity is etched or drilled into a substrate.

129. The miniature light source of claim 128, wherein said substrate includes an electrically insulating layer and an electrically conducting layer.

130. The miniature light source of claim 129, wherein said electrically insulating layer is made of a polymeric material.

131. The miniature light source of claim 121, wherein a sealing connection is made of indium.

132. The miniature light source of claim 127, wherein said piezoelectric layer is made of PVDF.

133. The miniature light source of claim 127, wherein said cavity is circular in cross section.

134. The miniature light source of claim 127, wherein said cavity is elliptic in cross section.

135. The miniature light source of claim 128, wherein said substrate includes a plurality of cell members.

136. The miniature light source of claim 121, wherein at least one of said first and second electrodes is specifically shaped so as to provide a maximal electrical output.

137. The miniature light source of claim 121, further comprising a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

138. The miniature light source of claim 137, wherein the bead is generally spherical an less than 5 mm in diameter.

139. The miniature light source of claim 137, wherein the bead is generally semi-spherical, less than 5 mm in diameter and less than 2.5 mm in height.

140. The miniature light source of claim 121, wherein said source of light is selected from the group consisting of a LED, a fluorescent light source, an electroluminescent source and a LD.

141. The miniature light source of claim 121, further comprising a light diffuser disposed to diffuse the light emitted by the source of light.

142. The miniature light source of claim 141, wherein said light diffuser is a lens disposed to diffuse the light emitted by the source of light.

143. A system for providing light of a desired wavelength, several discrete wavelengths or waveband to a treatment site disposed internally within a patient's body, to effect a photodynamic therapy of the treatment site, comprising:
(a) a miniature light source which comprises:
  (i) a source of light that produces light of a desired wavelength, several discrete wavelengths or waveband when energized by an electrical current;
  (ii) a rechargeable energy storage device operably coupled via an electrical circuit to said source of light;
  (iii) an acoustic transducer coupled to said rechargeable energy storage device, said acoustic transducer being activatable upon acoustic signal by an external acoustic energy source for recharging said rechargeable energy storage device; and
(b) said external acoustic energy source for recharging said rechargeable energy storage device.

144. The system of claim 143, wherein said rechargeable energy storage device is selected from the group consisting of a rechargeable battery and a capacitor.

145. The system of claim 143, wherein said miniature light source further comprising a rectifier that is connected to the acoustic transducer, said rectifier converting an alternating current to a direct current, which is supplied to said rechargeable energy storage device.

146. The system of claim 143, wherein the miniature light source is preprogrammed to shut off a predetermined time period following its activation.

147. The system of claim 143, wherein the miniature light source shuts off following a reception of an external shut off signal.

148. The system of claim 143, wherein the acoustic transducer comprises:
a cell member having a cavity;
a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
a first electrode attached to the external surface and a second electrode attached to the internal surface.

149. The system of claim 143, wherein said acoustic transducer comprises a transducer element adapted for converting acoustic wave energy transmitted through an external fluid medium into electric energy, said transducer element comprising:
a cell member having a cavity;
a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and
a first electrode attached to said external surface and a second electrode attached to said internal surface.

150. The system of claim 149, wherein said cavity is etched or drilled into a substrate.

151. The system of claim 150, wherein said substrate includes an electrically insulating layer and an electrically conducting layer.

152. The system of claim 151, wherein said electrically insulating layer is made of a polymeric material.

153. The system of claim 143, wherein a sealing connection is made of indium.

154. The system of claim 149, wherein said piezoelectric layer is made of PVDF.

155. The system of claim 149, wherein said cavity is circular in cross section.

156. The system of claim 149, wherein said cavity is elliptic in cross section.

157. The system of claim 150, wherein said substrate includes a plurality of cell members.

158. The system of claim 149, wherein at least one of said first and second electrodes is specifically shaped so as to provide a maximal electrical output.

159. The system of claim 143, wherein the miniature light source further comprises a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

160. The system of claim 159, wherein the bead is generally spherical and less than 5 mm in diameter.

161. The system of claim 159, wherein the bead is generally semi-spherical, less than 5 mm in diameter and less than 2.5 mm in height.

162. The system of claim 143, wherein said source of light is selected from the group consisting of a LED, a fluorescent light source, an electroluminescent source and a LD.

163. The system of claim 143, wherein the miniature light source further comprises a light diffuser disposed to diffuse the light emitted by the source of light.

164. The system of claim 163, wherein said light diffuser is a lens disposed to diffuse the light emitted by the source of light.

165. A method for providing light of a desired wavelength, several discrete wavelengths or waveband to an internal treatment site to effect a photodynamic therapy, comprising:

(a) providing a miniature light source which comprises:
(i) a source of light that produces light of a desired wavelength, several discrete wavelengths or waveband when energized by an electrical current;
(ii) a rechargeable energy storage device operably coupled via an electrical circuit to said source of light;
(iii) an acoustic transducer coupled to said rechargeable energy storage device, said acoustic transducer being activatable upon acoustic signal by an external acoustic energy source for recharging said rechargeable energy storage device;

(b) implanting said miniature light source at the internal treatment site of a subject in need thereof; and (c) recharging said rechargeable energy storage device via said acoustic transducer and said external acoustic energy source.

166. The method of claim 165, wherein said rechargeable energy storage device is selected from the group consisting of a rechargeable battery and a capacitor.

167. The method of claim 165, further comprising administering to the subject a therapeutically effective amount of a photodynamic therapy agent.

168. The method of claim 165, wherein the miniature light source is preprogrammed to shut off a predetermined time period following its activation.

169. The method of claim 165, wherein the miniature light source shuts off following a reception of an external shut off signal.

170. The method of claim 165, wherein said miniature light source further comprising a rectifier that is connected to the acoustic transducer, said rectifier converting an alternating current to a direct current, which is supplied to said rechargeable energy storage device.

171. The method of claim 165, wherein the miniature light source further comprises a biocompatible, light transmitting, acoustic energy transmitting, material that encloses said source of light and said acoustic transducer, to form a bead, said bead being thus adapted for insertion into the internal treatment site to effect the photodynamic therapy by providing light to the treatment site.

172. The method of claim 171, wherein the bead is generally spherical and less than 5 mm in diameter.

173. The method of claim 171, wherein the bead is generally semi-spherical, less than 5 mm in diameter and less than 2.5 mm in height.

174. The method of claim 165, wherein said source of light is selected from the group consisting of a LED, a fluorescent light source, an electroluminescent source and a LD.

175. The method of claim 165, wherein the miniature light source further comprises a light diffuser disposed to diffuse the light emitted by the source of light.

176. The method of claim 175, wherein said light diffuser is a lens disposed to diffuse the light emitted by the source of light.

177. The method of claim 165, wherein implanting said miniature light source at the internal treatment site is effected by injection or catheterization.

178. The method of claim 177, wherein said injecting comprises inserting a distal end of a needle that is connected to a syringe containing the miniature light source into the treatment site, and forcing the bead from the syringe into the treatment site through the needle.

179. The method of claim 165, wherein activating said acoustic transducer via said external acoustic energy source is effected by placing said external acoustic energy source against a body portion of a treated subject and activating said external acoustic energy source.

180. The method of claim 165, further comprising injecting a plurality of miniature light sources into the treatment site at spaced-apart locations.

181. The method of claim 165, wherein the acoustic transducer comprises:
a cell member having a cavity;
a substantially flexible piezoelectric layer attached to the cell member, the piezoelectric layer having an external surface and an internal surface, the piezoelectric layer having predetermined dimensions for enabling fluctuations at its resonance frequency upon impinging of an external acoustic wave; and
a first electrode attached to the external surface and a second electrode attached to the internal surface.

182. The method of claim 165, wherein said acoustic transducer comprises a transducer element adapted for converting acoustic wave energy transmitted through an external fluid medium into electric energy, said transducer element comprising:
a cell member having a cavity;
a substantially flexible piezoelectric layer peripherally attached to said cell member so as to isolate said cavity from the external fluid medium, said cavity containing gas and having a substantially lower acoustic impedance than said external fluid medium, a central portion of said piezoelectric layer not rigidly affixed with respect to said cavity, said piezoelectric layer having an external surface and an internal surface, said piezoelectric layer featuring such dimensions so as to enable fluctuations thereof in-and-out of said cavity at its resonance frequency upon impinging of an acoustic signal transmitted through the external fluid medium, said resonance frequency determined by the physical dimensions of said cavity and said piezoelectric layer wherein the wavelength of the acoustic signal is substantially larger than said dimensions; and
a first electrode attached to said external surface and a second electrode attached to said internal surface.

183. The method of claim 182, wherein said cavity is etched or drilled into a substrate.

184. The method of claim 183, wherein said substrate includes an electrically insulating layer and an electrically conducting layer.

185. The method of claim 184, wherein said electrically insulating layer is made of a polymeric material.

186. The method of claim 182, wherein said piezoelectric layer is made of PVDF.

187. The method of claim 182, wherein said cavity is circular in cross section.

188. The method of claim 182, wherein said cavity is elliptical in cross section.

189. The method of claim 183, wherein said substrate includes a plurality of cell members.

190. The method of claim 182, wherein at least one of said first and second electrodes is specifically shaped so as to provide a maximal electrical output.

* * * * *